(12) United States Patent
Kenley et al.

(10) Patent No.: US 8,080,528 B2
(45) Date of Patent: Dec. 20, 2011

(54) COMPOSITIONS AND METHODS FOR TREATMENT OF CACHEXIA

(75) Inventors: Richard Kenley, Poway, CA (US); Jonas Ekblom, San Diego, CA (US); Mikhail Denissenko, Poway, CA (US)

(73) Assignee: The Releef Initiative, Poway, CA (US)

( * ) Notice: Subject to any disclaimer, the term of this patent is extended or adjusted under 35 U.S.C. 154(b) by 1146 days.

(21) Appl. No.: 11/614,056

(22) Filed: Dec. 20, 2006

(65) Prior Publication Data

US 2007/0149465 A1    Jun. 28, 2007

Related U.S. Application Data

(60) Provisional application No. 60/753,118, filed on Dec. 22, 2005, provisional application No. 60/772,752, filed on Feb. 13, 2006.

(51) Int. Cl.
*A61K 31/70* (2006.01)
(52) U.S. Cl. ......................................... 514/29
(58) Field of Classification Search ............... None
See application file for complete search history.

(56) References Cited

U.S. PATENT DOCUMENTS

| 5,750,493 | A | * | 5/1998 | Sommadossi et al. | 514/1 |
| 5,880,101 | A | | 3/1999 | Stankov | |
| 7,101,576 | B2 | * | 9/2006 | Hovey et al. | 424/490 |

FOREIGN PATENT DOCUMENTS

| EP | 0 308 157 A | 3/1989 |
| EP | 0 338 404 A | 10/1989 |
| WO | 2005/060693 A2 | 7/2007 |
| WO | 2008/004224 A2 | 1/2008 |

OTHER PUBLICATIONS

MacDonald et al "Understanding and Managing Cancer Cachexia", J. Am. Coll. Surg. vol. 197, No. 1, Jul. 2003, pp. 143-161.*
Stallion et al "Reversal of cancer cachexia in rats by cimaterol and supplemental nutrition", Surgery, Oct. 1991, vol. 110, No. 4, pp. 678-684 (Abstract).*
Stallion et al, "Reversal of cancer cachexia in rats by cimaterol and supplemental nutrition", Surgery, Oct. 1991, 110(4): 678-684.*
Yavuzen, T., et al., "Systematic Review of the Treatment of Cancer-Associated Anorexia and Weight Loss", J Clin Oncol 23.8500-8511 (2005).
Busquets, S., et al., "Anticachectic Effects of Formoterol: A Drug for Potential Treatment of Muscle Wasting", [Cancer Research 64, 6725-6731, Sep. 15, 2004.
Easton-Carter, K.L., et al., "Possible Roxithromycin-Induced Fulminant Hepatic Failure in a Child", Pharmacotherapy 2001;21(7):867-870.
Pirzada, O.M., et al., "Improved lung function and body mass index associated with long-term use of Macrolide antibiotics", Journal of Cystic Fibrosis 2 (2003) 69-71.
Carbo, N., et al., "Comparative effects of b2-adrenergic agonists on muscle waste associated with tumour growth", Cancer Letters 115 1997 113-118.
Sakamoto, M., et al., "Long-term clarithromycin treatment for cancer cachexia of inoperable non-small cell lung cancer patients", Japanese Journal of Chemotherapy, vol. 44, 1996. Abstract.
Sakamoto, M., et al., "Anti-cachectic effect of clarithromycin for patients with unresectable non-small cell lung cancer", Chemotherapy, Dec. 2001.
Hori, S., et al., "Effect of clarithromycin on lipopolysaccharide-induced anorexia", The Japanese journal of antibiotics, Dec. 2001.
Sakamoto, M., et al., "Efficacy of clarithromycin on cancer cachexia in patients with primary non-small cell lung cancer", The Japanese journal of antibiotics, Mar. 1997.
Antonio Pascal Lopez, et al., "Systematic Review of megestrol acetate in the treatment of anorexia-cachexia syndrome", J. Pain and Symptom Management 27(4):360-369 2004.
Main, B.W., et al., "Cardiovascular effects of the macrolide antibiotic tilmicosin, administered alone and in combination with propanolol or dobutamine, in consious unrestrained dogs", J. Veterinary Pharmacology and Therapeutics 19:225-232 1996.
Extended European Patent Office Search Report, dated Oct. 30, 2009.

* cited by examiner

*Primary Examiner* — Elli Peselev
(74) *Attorney, Agent, or Firm* — David P. Lentini

(57) ABSTRACT

Compositions and methods for preventing and treating wasting disorders, such as cachexia and anorexia, are provided. In one aspect, the present invention provides a method for preventing and treating a wasting disorder in a mammal. In one embodiment, the method of the invention comprises administering to such mammal a macrolide and a $\beta_2$-adrenergic agonist in combination such that the macrolide and said $\beta_2$-agonist are administered in amounts effective to prevent or at least alleviate said wasting disorder.

3 Claims, 1 Drawing Sheet

COMPOSITIONS AND METHODS FOR TREATMENT OF CACHEXIA

1 CROSS-REFERENCE TO RELATED APPLICATIONS

Figure 1:
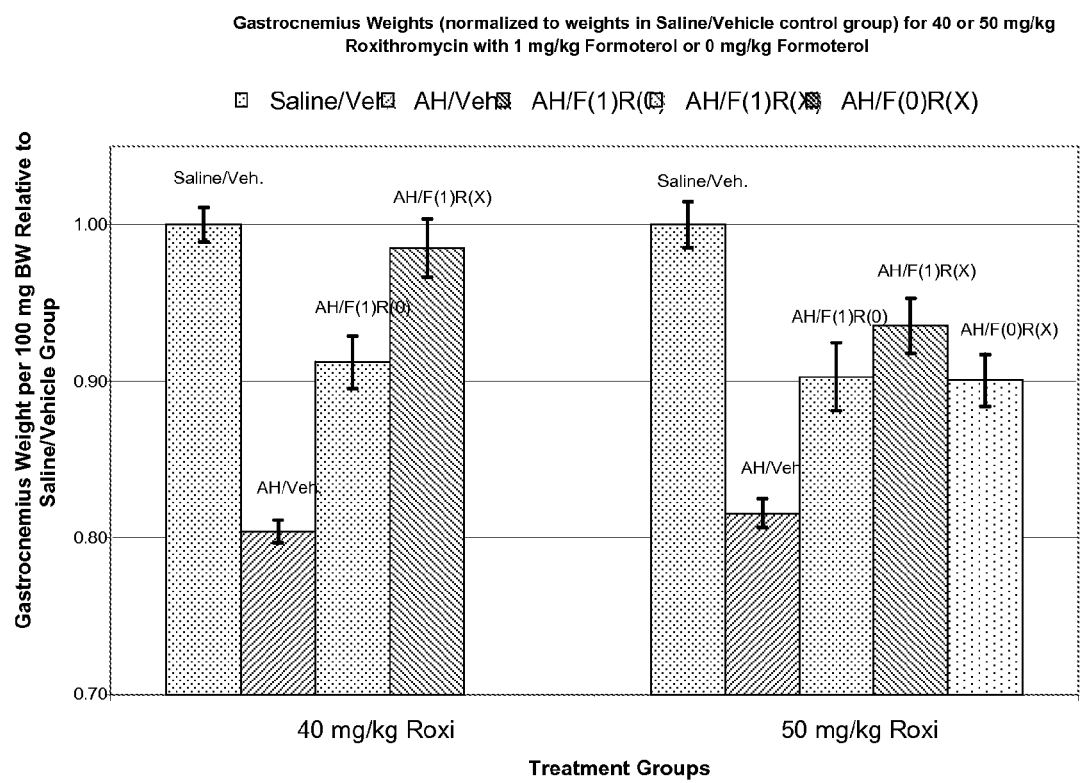

This application claims priority under 35 U.S.C. §119(e) from provisional U.S. patent applications Ser. Nos.: 60/753,118, filed 22 Dec. 2005; and 60/772,752, filed 13 Feb. 2006. The disclosures of these applications are incorporated herein by reference in their entireties and for all purposes.

2 BACKGROUND OF THE INVENTION

2.1 Field of the Invention

The present invention relates to compositions and methods for preventing and treating metabolic disorders, especially disorders characterized by pathologic loss of appetite, adipose tissue, and lean body mass. More specifically, the present invention relates to compositions and methods for preventing and treating cachexia, especially cachexia associated with cancer and chronic renal insufficiency (CRI). The invention has relevance to the fields of biology, medicine, oncology, and pharmacology.

2.2 The Related Art

Catabolic wasting, or cachexia, is a syndrome characterized by: involuntary, progressive loss of both fat and skeletal muscle, refractoriness of weight loss to increased nutritional input, elevated resting energy expenditure (REE), decreased protein synthesis, altered carbohydrate metabolism (increased Cori cycle activity), hyper-catabolism of muscle via the ATP-ubiquitin-dependent proteasome pathway of proteolysis, and of adipose tissue via lipolysis (Body J J, Curr Opin Oncol 11:255-60, 1999, Muscaritoli M, et al: Eur J Cancer 42:31-41, 2006). Typically, at least 5% or 5 pounds of pre-illness body weight must have been lost before a patient is diagnosed with cachexia. Roughly half of all cancer patients experience some degree of catabolic wasting, with a higher occurrence seen in cases of malignancies of the lung, pancreas, and gastrointestinal tract (Dewys W D, et al: Am J Med 69:491-7, 1980). The syndrome is also found in patients having immunodeficiency disorders, such as AIDS, as well patients suffering bacterial and parasitic diseases, rheumatoid arthritis, and chronic diseases of the bowel, liver, kidneys, lungs, and heart. Cachexia is also associated with anorexia and can manifest as a condition in aging or as a result of physical trauma and burn injuries. The cachexia syndrome diminishes the patient's functional ability and quality of life, worsens the underlying condition and reduces tolerance to medications. The degree of cachexia is inversely correlated with the survival time of patients and it always implies a poor prognosis. In recent years, age-related diseases and disabilities have become of major health interest and importance.

Anorexia, a medical term for appetite loss, is a debilitating manifestation of many malignancies, and is observed in patients with cancer, infectious diseases, chronic organ failure, and trauma. Anorexia is a serious syndrome, because it leads to reduced caloric intake and malnutrition. Manifestations of anorexia include a decreased sense of taste and smell of food, early satiety, a decreased sense of hunger, and even outright aversion to food. Nausea and vomiting may be symptomatic as well. The etiology of anorexia is poorly understood; and effective treatment options are limited. Some studies suggest that a combination of hormonal, social, and psychological reasons may be important factors in the development and progression of the syndrome.

Despite the fact that cachexia is often associated with cancer, no consistent relationship has been demonstrated between the development of cachexia and tumor size, disease stage, and the type or duration of the malignancy. However, cancer cachexia is commonly associated with: reduced caloric intake, an increase in resting energy expenditure, and alterations in protein, fat, and carbohydrate metabolism. For example, some noted abnormalities in carbohydrate metabolism include: increased rates of total glucose turnover, increased hepatic gluconeogenesis, glucose intolerance and elevated glucose levels. Increased lipolysis, increased free fatty acid and glycerol turnover, hyperlipidemia, and reduced lipoprotein lipase activity are frequently noted as well. Importantly, the weight loss associated with cancer cachexia is caused not only by a reduction in body fat stores, but also by a reduction in total body protein mass and extensive skeletal muscle wasting. Increased protein turnover and poorly regulated amino acid oxidation may also be important factors in the progression of the syndrome. In addition, certain host-derived factors that are produced in response to the cancer, e.g., pro-inflammatory cytokines (tumor necrosis factor-$\alpha$ (TNF-$\alpha$), interleukin-1, interleukin-6, and $\gamma$-interferon), acute phase proteins (such as C-reactive protein), and certain prostaglandins also seem to be associated with cancer cachexia.

In regards to cachexia associated with renal dysfunction, the basic pathophysiology is poorly understood. Chronic renal insufficiency (CRI) may result from any major cause of renal dysfunction. The most common cause of end-stage renal disease is diabetic nephropathy, followed by hypertensive nephroangiosclerosis and various primary and secondary glomerulopathies. There is a high prevalence of protein-energy malnutrition in both non-dialyzed patients with advanced chronic renal failure and in those individuals with end-stage renal disease who are receiving maintenance hemodialysis or chronic peritoneal dialysis therapy. The high prevalence of cachexia and malnutrition is of major concern because markers of protein-energy malnutrition are strong predictors of morbidity and mortality. Up to 40% of patients with chronic renal failure requiring hemodialysis or long-term peritoneal dialysis reportedly present weight loss and are associated with increased morbidity and mortality rates. Decreased levels of nitrogen stores and body weight and depleted visceral protein stores of albumin and transferrin are observed. Causes for malnutrition are multifactorial and include blood loss, protein and other nutrient loss during dialysis, catabolism due to chronic illness, and anorexia due to altered taste sensation, suboptimal oral intake, and depression (Kalantar-Zadeh K: Semin Dial 18:365-9, 2005).

Current methods for treating cachexia and anorexia have only limited benefit at best. As summarized by Yavusen (Yavuzsen T, et al: J Clin Oncol 23:8500-11, 2005), examples of randomized controlled clinical trials that yielded negative, mixed, or inconclusive results include trials with: Hydrazine sulfate, Cyproheptadine, Pentoxifylline, Melatonin, Erythropoietin with and without Indomethacin, Eicosapentaenoic Acid, Androgenic Steroids, Ghrelin, Interferon, and Dronabinol. Of all the drugs reviewed, only two types, corticosteroids and progestins, demonstrated consistently positive results in multiple randomized, controlled, clinical trials.

In particular the progesterone derivative, megestrol acetate, has been shown to increase appetite and weight (but not quality of life, survival, or functional ability) in cancer cachexia patients. Megestrol acetate and/or its metabolites may, either directly or indirectly, stimulate appetite, resulting in weight gain, or may alter metabolic pathways via interference with the production or action of mediators such as tumor necrosis factor-α. Evidence from clinical studies indicates that the increase in body weight observed during megestrol acetate therapy is related to the drug's appetite-stimulant or metabolic effects rather than its glucocorticoid-like effects or the production of edema.

The administration of $\beta_2$-adrenergic-agonists ("$\beta_2$-agonists") is known to be associated with anabolic effects in humans (Choo J J, Horan M A, Little R A, et al, Am J Physiol 263:E50-6, 1992). The $\beta_2$-agonists increase lean body mass by increasing protein synthesis and by interfering with the ATP-dependent ubiquitin-proteasome pathway (Lambert CP, Uc EY, Evans W J: Pharmacotherapy of Cachexia:311-324, 2005). Clinical trials have shown that $\beta_2$-agonists can increase lean body mass in healthy athletes (Caruso J, Hamill J, Yamauchi M, et al: JAppl Physiol98:1705-11, 2005, Caruso J F, et al: Med Sci Sports Exerc 27:1471-6, 1995, Martineau L, et al: Clin Sci (Lond) 83:615-21, 1992), and in patients suffering from muscular dystrophy (Kissel J T, et al: Neurology 57:1434-40, 2001). $\beta_2$-agonists administered by injection to rats and mice bearing highly cachectic tumors reportedly reduced or reversed muscle wasting (Busquets S et al., Cancer Res 64:6725 31 (2004); Carbo N et al., Cancer Lett 115:113 8 (1997); Costelli P et al., J Clin Invest 95:2367 72 (1995); Piffar P M et al., Cancer Lett 201:139-48 (2003)). Surprisingly, however, $\beta_2$-agonists have not been studied in humans for prevention or treatment of cachexia in cancer or CRI. Furthermore, the $\beta_2$-agonist, formoterol fumarate, specifically when administered via oral ingestion, has never been studied in either animals or in humans for prevention or treatment of cachexia in cancer, CRI., or ageing sarcopenia. This latter observation is surprising insofar as formoterol fumarate is known to be orally bioavailable, and the oral route of administration affords significant benefits over other routes of administration (such as intraperitoneal injection, or inhalation) with respect to patient convenience and compliance. It is also surprising that formoterol fumarate has never been studied as a anti-cachectic preventive measure in either mammals or humans, because the anabolic effects of the drug should be effective in increasing the lean body mass and strength of individuals who are at risk of cachexia or who suffer from "pre-cachectic" metabolic imbalances but who have not yet suffered significant involuntary wasting.

Because cancer cachexia is associated with elevated levels of pro-inflammatory cytokines (TNF-α, IL6, CRP, and so forth), prior clinical studies have suggested that non-steroidal anti-inflammatory drugs (NSAIDs) such as ibuprofen (Mc-Millan D C, et al: Br J Cancer 79:495-500, 1999), and indomethacin (Lundholm K, et al: Cancer Res 54:5602-6, 1994) can have beneficial effects. Macrolide antibiotics structurally-related to erythromycin are also known to possess anti-inflammatory properties (Amsden G W: J Antimicrob Chemother 55:10-21, 2005). Anti-inflammatory macrolides include clarithromycin, roxithromycin, and azithromycin. In small, non-randomized, and non-controlled clinical studies, Sakamoto and coworkers (Mikasa K, et al: Chemotherapy 43:288-96, 1997, Sakamoto M et al., Chemotherapy 47:444-51 2001) reported that treating non-small-cell lung cancer patients with clarithromycin increased the median survival time, reduced IL6 serum levels, and increased body weight. Randomized, controlled clinical trials with macrolides in cancer cachexia patients, however, have not been performed, and the effects of macrolides on performance status, quality of life, and functional performance in cancer cachexia patients have not been reported.

In the case of CRI, Kalantar-Zadeh (Kalantar-Zadeh K, Stenvinkel P, Bross R, et al: Kidney insufficiency and nutrient-based modulation of inflammation. Curr Opin Clin Nutr Metab Care 8:388-96, 2005) has shown that patients have a high cardiovascular mortality rate and that protein-energy malnutrition and inflammation have been implicated as the main cause of both cachexia and high mortality in these patients. These workers note that in this medical field, there is no consensus as to how to correct malnutrition and inflammation CRI patients, and that the complexity of the disease will probably require multiple intervention modalities. A review by Basaria S, (Basaria S, Wahlstrom J T, Dobs A S. Clinical review 138: Anabolic-androgenic steroid therapy in the treatment of chronic diseases.J Clin Endocrinol Metab. 2001 Nov;86(11):5108-17) proposes treatment with anabolic-androgenic steroids for severe weight loss associated with chronic renal disease.

Cachexia and anorexia thus, remain a frustrating and deadly problem for clinicians and patients. Both animal and human studies suggest that nutritional support alone is largely ineffective in replenishing lean body mass in the cancer-bearing host. Randomized trials exploring the usefulness of total parenteral nutrition support as an adjunct to cytotoxic antineoplastic therapy have, demonstrated little improvement in treatment results. See for example Brennan, M. F., and Burt, M. E., 1981, Cancer Treatment Reports 65 (Suppl. 5): 67 68. This, along with a clear demonstration that total parenteral nutrition can stimulate tumor growth in animals suggests the routine use of total parenteral nutrition in cancer treatment is not justified (Visner, D. L., 1981, Cancer Treatment Reports 65 (Suppl 5): 12).

The generally unsatisfactory results of cancer cachexia studies trials undertaken in the past 15 years, and the growing understanding that tumor- and/or host-driven metabolic imbalances on the molecular level may be important before significant weight loss is evident combine to suggest that cachexia/anorexia interventions should be taken in advanced cancer patients at the time of initial diagnosis, whether or not the patients initially present with significant weight loss. Muscaritoli et al (2006) address this point as follows: "several of the metabolic, biochemical and molecular alterations currently believed to be responsible for the phenotypic features of cachexia are already present upon first cancer diagnosis, even in the absence of significant body weight loss. Thus, the consolidated view is that cancer cachexia should be regarded to as an "early phenomenon". The relevance of cancer cachexia in negatively affecting, not only patients' mortality, but also surgical risk, response to first- and second-line chemo-/radiotherapy, and not lastly quality of life, has progressively emerged during the recent years. Unfortunately, the predominant feature of cancer cachexia, i.e., the steadily progressive loss of muscle mass and function, has been shown to be only minimally reversible with the currently available nutritional, metabolic or pharmacological tools. Consequently, the development of early and effective interventions aimed at preventing rather than reversing the metabolic perturbations ultimately leading to muscle wasting and cachexia is now perceived as a mandatory need by the scientific community,"

Thus, there remains a need for better treatment options to help those suffering from cachexia and anorexia. There also remains a need to prevent the clinical manifestations of anorexia and cachexia from becoming significant in those individuals who are suffering from metabolic imbalances s associated with cachexia, but who have not yet experienced significant involuntary weight loss. The present invention addresses these and other needs.

3 SUMMARY OF THE INVENTION

The present invention provides methods and compositions to prevent and treat cachexia, anorexia, and other wasting disorders in mammals. Without being held to any particular theory of action, the methods and compositions of the invention are expected to improve the health of those suffering cachexia, anorexia, and other wasting disorders or at risk of suffering these wasting disorders by: decreasing the sufferer's levels of pro-inflammatory cytokines (IL-6 and TNF) and acute phase proteins (C-reactive protein) while also increasing protein synthesis and interfering with catabolic proteolysis, thereby increasing lean body mass. The present invention also provides improvements of quality of life for patients suffering from such conditions in terms of increased sense of well-being, enhanced appetite, decreased fatigue and improved strength, endurance, clinical performance status, and tolerance to medications.

In a first aspect, the present invention provides a method for preventing or treating a wasting disorder in a mammal. In one embodiment, the method of the invention comprises administering to such mammal a macrolide and a $\beta_2$-agonist in combination such that the macrolide and $\beta_2$-agonist are administered in amounts effective to prevent or at least alleviate the wasting disorder when administered in combination. In another embodiment, the method of the invention includes administering a pharmaceutically effective amount of a non-steroidal anti-inflammatory agent in addition to the macrolide and $\beta_2$-agonist. In some of these embodiments, the non-steroidal anti-inflammatory agent is a non-selective cyclo-oxygenase inhibitor, such as aspirin, diclofenac, naproxen, or indomethacin, or ibuprofen; or a selective cyclo-oxygenase-2 (COX-2) inhibitor, such as celecoxib, valdecoxib, rofecoxib or meloxicam. Thus, in some embodiments, the methods of the present invention provide for an anti-inflammatory and anabolic agent combination to be administered as an adjunct to an appetite stimulating agent to assist mammals receive adequate nutritional intake.

In one more specific embodiment, the method of the invention further includes administering a pharmaceutically effective amount of an appetite-stimulating steroid. As used herein, an "appetite-stimulating steroid" is a synthetic version of a natural hormone that enhances appetite. In some embodiments, the A-ring of the appetite-stimulating steroids possesses a non-aromatic A-ring and a keto group at the 3-position of the steroid's carbon skeleton. Such steroids can be modified to facilitate delivery by peroral, transdermal patches, buccal or intranasal delivery. In a more particular embodiment, the appetite-stimulating steroid is megestrol acetate. In some embodiments, the megestrol acetate is administered at a dose between about 100 mg/d and about 1,200 mg/d; more particularly, between about 100 mg/d and about 1,000 mg/d; and still more particularly, between about 400 mg/d and about 1,200 mg/d.

In some embodiments, the macrolide and $\beta_2$-agonist have no substantial pharmacological interaction. In more particular embodiments the macrolide and $\beta_2$ agonist have serum half-live values differing by less than about 70%, by less than about 50%, and by less than about 30%. In sill other embodiments, the macrolide and $\beta_2$-agonist have substantially different clearance mechanisms. The macrolide and $\beta_2$-agonist can be administered in the same or different pharmaceutical carriers.

In some embodiments, the macrolide is roxithromycin, clarithromycin, or azithromycin. In more particular embodiments, the macrolide is roxithromycin. In still more particular embodiments, the macrolide is roxithromycin, and the roxithromycin is administered at a dose between about 25 mg/d and about 750 mg/d. In other embodiments, the macrolide is roxithromycin, and the roxithromycin is administered at a dose between 50 mg/d and about 300 mg/d. In still other embodiments, the macrolide is roxithromycin, and the roxithromycin is administered at a dose between about 50 mg/d and about 200 mg/d. In yet other embodiments, the macrolide is roxithromycin, and the roxithromycin is administered at a dose between about 150 mg/d and about 750 mg/d.

In some embodiments, the $\beta_2$-agonist is formoterol fumarate, bambuterol, or albuterol. In more specific embodiments, the $\beta_2$-agonist is formoterol fumarate. Among the embodiments in which the $\beta_2$-agonist is formoterol fumarate, some embodiments of the invention include those in which the formoterol fumarate is administered at a dose between approximately 5 µg/d and approximately 500 µg/d and between approximately 5 µg/d and approximately 240 µg/d.

In a second aspect, the present invention provides a pharmaceutical composition for preventing and treating a wasting disorder in a mammal, comprising a macrolide and a $\beta_2$-agonist in combination in a pharmaceutically acceptable carrier. The macrolide and $\beta_2$-agonist are provided in amounts effective to prevent or at least alleviate said wasting disorder when administered in combination.

In some embodiments, the macrolide and $\beta_2$-agonist have no substantial pharmacological interaction. In more particular embodiments the macrolide and $\beta_2$-agonist have serum half-live values differing by less than about 70%, by less than about 50%, and by less than about 30%. In sill other embodiments, the macrolide and $\beta_2$-agonist have substantially different clearance mechanisms. The macrolide and $\beta_2$-agonist can be administered in the same or different pharmaceutical carriers.

In some embodiments, the macrolide is roxithromycin, clarithromycin, or azithromycin. In more particular embodiments, the macrolide is roxithromycin. In still more particular embodiments, the macrolide is roxithromycin, and the roxithromycin in provided in an amount sufficient to deliver to such mammal a dose between about 25 mg/d and about 750 mg/d. In other embodiments, the macrolide is roxithromycin, and the roxithromycin in provided in an amount sufficient to deliver to such mammal a dose between 50 mg/d and about 300 mg/d. In still other embodiments, the macrolide is roxithromycin, and the roxithromycin in provided in an amount sufficient to deliver to such mammal a dose between about 50 mg/d and about 200 mg/d. In yet other embodiments, the macrolide is roxithromycin, and the roxithromycin in provided in an amount sufficient to deliver to such mammal a dose between about 150 mg/d and about 750 mg/d.

In some embodiments, the $\beta_2$-agonist is formoterol fumarate, bambuterol, or albuterol. In more specific embodiments, the $\beta_2$-agonist is formoterol fumarate. Among the embodiments in which the $\beta_2$-agonist is formoterol fumarate, some embodiments of the invention include those in which the formoterol fumarate in provided in an amount sufficient to deliver to such mammal a dose between about 5 µg/d and about 500 µg/d and between about 5 µg/d and about 240 µg/d.

In a third aspect, the present invention provides a method for preventing and treating a wasting disorder in a mammal, comprising administering to such mammal a macrolide such as roxithromycin, in an amount effective to prevent or at least alleviate said wasting disorder.

In a fourth aspect, the present invention provides a method and compositions for preventing and treating a wasting disorder in a mammal, comprising administering to such mammal a $\beta_2$-agonist, such as formoterol fumarate, formulated in a dosage form suitable for oral administration and in an amount effective to prevent or at least alleviate said wasting disorder.

These and other aspects and advantages will become apparent when the Description below is read in conjunction with the accompanying Drawings.

4 BRIEF DESCRIPTION OF THE DRAWINGS

FIG. 1 illustrates the effects of 40 mg/kg and 50 mg/kg roxithromycin (with and without 1 mg/kg formoterol fumarate) on gastrocnemius muscle in AH-inoculated rats.

5 DESCRIPTION OF SOME EMBODIMENTS OF THE INVENTION

In a first aspect, the present invention provides methods for preventing and treating a wasting disorder in a mammal, comprising administering to such mammal a macrolide and a $\beta_2$-agonist in combination. The macrolide and the $\beta_2$-agonist are administered in amounts effective to prevent or at least alleviate said wasting disorder when administered in combination. In some embodiments of the just recited method, the macrolide and the $\beta_2$-agonist are administered in separate pharmaceutically acceptable carriers. In other embodiments of the just recited method, the macrolide and $\beta_2$-agonist are administered in the same pharmaceutically acceptable carrier. The choice and preparation of pharmaceutical compositions suitable for use in the present invention in which the two agents are administered either separately or in combination will be known to those having ordinary skill in the art.

In another embodiment, the method of the invention includes administering a pharmaceutically effective amount of a non-steroidal anti-inflammatory agent in addition to the macrolide and $\beta_2$-agonist. In some of these embodiments, the non-steroidal anti-inflammatory agent is a non-selective cyclo-oxygenase inhibitor, such as aspirin, diclofenac, naproxen, or indomethacin, or ibuprofen; or a selective cyclo-oxygenase-2 (COX-2) inhibitor, such as celecoxib, valdecoxib, rofecoxib or meloxicam. Thus, in some embodiments, the methods of the present invention provide for an anti-inflammatory and anabolic agent combination to be administered as an adjunct to an appetite stimulating agent to assist mammals receive adequate nutritional intake.

Suitable macrolides include those known to have useful anti-inflammatory properties. Examples of suitable macrolides include roxithromycin, clarithromycin, or azithromycin. One particular example is roxithromycin. In some embodiments of the present invention, the macrolide is roxithromycin, and the roxithromycin is administered at a dose between about 25 mg/d and about 750 mg/d. In other embodiments, the macrolide is roxithromycin, and the roxithromycin is administered at a dose between about 50 mg/d and about 300 mg/d. In still other embodiments, the macrolide is roxithromycin, and the roxithromycin is administered at a dose between about 50 mg/d and about 200 mg/d. In yet other embodiments, the macrolide is roxithromycin, and the roxithromycin is administered at a dose between about 150 mg/d and about 750 mg/d. Sources and methods for identifying, obtaining, and preparing suitable dosage forms for the macrolide used in the method of the invention will be apparent to those having ordinary skill in the art.

Suitable $\beta_2$-agonists include: bambuterol, albuterol, bitolterol, formoterol fumarate, isoetharine, isoproterenol, metaproterenol, pirbuterol, ritodrine, salmeterol, benzenedimethanol, and terbutaline. In some embodiments, the $\beta_2$-agonist is formoterol fumarate, bambuterol, or albuterol. In more particular embodiments, the $\beta_2$-agonist is formoterol fumarate. In still more particular embodiments, the $\beta_2$-agonist is formoterol fumarate administered at a dose between about 5 µg/d and about 500 µg/d. In still other more particular embodiments, the $\beta_2$-agonist is formoterol fumarate administered at a dose between about 5 µg/d and about 240 µg/d. Sources and methods for identifying, obtaining, and preparing suitable dosage forms for the $\beta_2$-agonists used in the method of the invention will be apparent to those having ordinary skill in the art.

In some embodiments, the macrolide and the $\beta_2$-agonist have no substantial pharmacological interaction. In more specific embodiments, these two components have serum half-live values differing by less than about 70%. In other more specific embodiments, these two components have serum half-live values differing by less than about 50%. In still other more specific embodiments, these two components have serum half-live values differing by less than about 30%. In yet other more specific embodiments, these two components have substantially different clearance mechanisms. The determination of suitable serum half-lives and clearance mechanisms can be performed by those having ordinary skill in the art.

In other embodiments, the method of the present invention includes administering any one of the foregoing combinations in conjunction with administering a pharmaceutically effective amount of an appetite-stimulating steroid. In a more particular embodiment, the method of the present includes administering any one of the foregoing combinations in conjunction with administering a pharmaceutically effective amount of megestrol acetate. In some embodiments that include administering any one of the foregoing combinations in conjunction with megestrol acetate, the megestrol acetate is administered at a dose between about 100 mg/d and about 1,200 mg/d. In other embodiments that include administering any one of the foregoing combinations in conjunction with megestrol acetate, the megestrol acetate is administered at a dose between about 100 mg/d and about 1,000 mg/d. In still other embodiments that include administering any one of the foregoing combinations in conjunction with megestrol acetate, the megestrol acetate is administered at a dose between about 400 mg/d and about 1,200 mg/d. The megestrol acetate, macrolide, and $\beta_2$-agonist may be administered as a combination in a single pharmaceutically-acceptable carrier, or co-administered in individual, separate pharmaceutical carriers.

In another aspect, the present invention provides pharmaceutical composition for preventing and treating a wasting disorder in a mammal, comprising a macrolide and a $\beta_2$-agonist in combination in a pharmaceutically acceptable carrier. The macrolide and the $\beta_2$-agonist are provided in amounts effective to prevent or at least alleviate said wasting disorder when administered in combination.

The macrolide and $\beta_2$-agonist are chosen in accordance with the considerations provided above. In some embodiments, macrolide and the $\beta_2$-agonist have no substantial pharmacological interaction. More particular embodiments include those in which the macrolide and the $\beta_2$-agonist have serum half-live values differing by less than about 70%. Other embodiments include those in which the macrolide and the $\beta_2$-agonist have serum half-live values differing by less than about 50%. Still other embodiments include those in which the macrolide and the $\beta_2$-agonist have serum half-live values differing by less than about 30%. In still other embodiments, the macrolide and the $\beta_2$-agonist have substantially different clearance mechanisms. Sources and methods for identifying, obtaining, and preparing suitable dosage forms for the macrolide and $\beta_2$-agonist used in the method of the invention will be apparent to those having ordinary skill in the art.

In some embodiments of the composition of the invention, the macrolide is roxithromycin, azithromycin, or clarithromycin. In more particular embodiments, the macrolide is roxithromycin. In still more particular embodiments, macrolide is roxithromycin, and the roxithromycin in provided in an amount sufficient to deliver to such mammal a dose between about 50 mg/d and about 750 mg/d. In other more particular embodiments, macrolide is roxithromycin, and the roxithromycin in provided in an amount sufficient to deliver to such mammal a dose between about 50 mg/d and about 300 mg/d. In yet other more particular embodiments, macrolide is roxithromycin, and the roxithromycin in provided in an amount sufficient to deliver to such mammal a dose between about 50 mg/d and about 200 mg/d. In still other more particular embodiments, macrolide is roxithromycin, and the roxithromycin in provided in an amount sufficient to deliver to such mammal a dose between about 150 mg/d and about 750 mg/d. Sources and methods for identifying, obtaining, and preparing suitable dosage forms will be apparent to those having ordinary skill in the art.

Suitable $\beta_2$-agonists include: albuterol, bitolterol, formoterol fumarate, isoetharine, isoproterenol, metaproterenol, pirbuterol, ritodrine, salmeterol, benzenedimethanol, and terbutaline. In some embodiments of the composition of the invention, the $\beta_2$-agonist is formoterol fumarate, bambuterol, or albuterol. However, -blockers are not included as suitable agents. In more particular embodiments, the $\beta_2$-agonist is formoterol fumarate. In still more particular embodiments, the $\beta_2$-agonist is formoterol fumarate, and the formoterol fumarate in provided in an amount sufficient to deliver to such mammal a dose between about 5 µg/d and about 240 µg/d. In other more particular embodiments, the $\beta_2$-agonist is formoterol fumarate, and the formoterol fumarate in provided in an amount sufficient to deliver to such mammal a dose between about 5 µg/d and about 40 µg/d. Sources and methods for identifying, obtaining, and preparing suitable dosage forms will be apparent to those having ordinary skill in the art.

In a third aspect, the present invention provides a method for preventing and treating a wasting disorder in a mammal, comprising administering to such mammal roxithromycin in an amount effective to prevent or at least alleviate said wasting disorder.

The methods and compositions described herein are suitable for both humans and animals, especially animals of great economic or emotional value, such as, but not limited to: horses, cows, sheep, goats, pigs, cats, dogs, and the like, whether mature or immature (i.e., adults and children).

The compositions and methods described herein are administered in amounts and at a frequency sufficient to prevent or at least alleviate the wasting disorder. In one embodiment, a patient suffering from or at risk of developing a wasting disorder is treated using the methods and compositions described herein once per day. In another embodiment, a patient suffering from or at risk of developing a wasting disorder is treated using the methods and compositions described herein twice per day. The dosage form can be any form suitable to deliver a therapeutically effective dose (i.e., a dose sufficient to at least alleviate the wasting disorder, including an amount of an active pharmaceutical ingredient as described herein).

Patient progress can be determined by measuring and observing relevant changes in the patient's appearance (e.g., visible and measurable changes in body mass), body composition (e.g. lean body mass), patient functionality (e.g., in exercise tests of strength and endurance), and by determining relevant clinical markers. Examples of such markers include, without limitation: levels of pro-inflammatory cytokines (IL-6 and TNF) and acute phase proteins (C-reactive protein), lean body mass, ergonomic performance, strength, clinical performance status, and quality of life. The determination, measurement, and evaluation of such characteristics and markers associated with clinical progress are known to those having ordinary skill in the art.

In another aspect, the present invention also provides methods for preventing significant weight loss in a mammal that is at risk of entering a cachectic and/or anorexic state because of an underlying pathology (cancer, AIDS, CRI, etc), or due to the presence of an altered metabolic process (such as muscle hypercatabolism) or an inflammatory condition (such as elevated levels of IL6, TNF, or CRP). In these embodiments, any of the compositions and dosing regimens provided by the invention are administered to a mammal susceptible to entering, or experiencing the metabolic and inflammatory imbalances associated with a cachectic or anorexic state to delay thereby the onset of cachexic or anorexic symptoms, or retard the progression of a cachectic or anorexic state in an individual. The determination of any of these conditions can be determined using knowledge available to those having ordinary skill in the art, such as the detection of significant weight loss (e.g., a loss of more than about 5% average normal weight), above-normal levels of inflammatory markers (e.g., IL6, TNF-$\alpha$, C-reactive protein), or elevated levels of mRNA associated with ubiquitin-proteasome proteolysis, or some combination thereof in an individual. In these embodiments, the patient undergoing treatment using the methods and compositions provided by the invention is expected to better tolerate the treatment regimen(s) being used to address the underlying cause of the cachectic or anorexic state, such as chemotherapy, radiation therapy, bone marrow transplant, and the like, which treatment regimen(s) those having ordinary skill in the art recognize must be administered according to a strict schedule to achieve maximal therapeutic effect.

In some embodiments the $\beta_2$-agonist and the macrolide are co-administered in separate pharmaceutical carriers. Among the embodiments in which the $\beta_2$-agonist is separately administered, the pharmaceutical carrier is a liquid (solution, syrup, emulsion, or suspension) suitable for oral ingestion or enteral administration using a naso-gastric tube. In other embodiments, the pharmaceutical carrier is a liquid (solution, suspension, or emulsion) suitable for parenteral injection of the $\beta_2$-agonist. In still other embodiments the pharmaceutical carrier is a solid or semi-solid (e.g., powder, sachet, tablet or capsule) dosage form suitable for oral ingestion that provides for immediate release of the $\beta_2$-agonist into the gastric compartment. In other embodiments, the pharmaceutical carrier is a solid or semi-solid (powder, sachet, tablet or capsule) dosage form suitable for oral ingestion that provides for prolonged or controlled or sustained release of the $\beta_2$-agonist into the gastric compartment. Among the embodiments in which the macrolide is separately administered, the pharmaceutical carrier is a liquid (solution, syrup, emulsion, or suspension) suitable for oral ingestion or enteral administration using a naso-gastric tube. In other embodiments, the pharmaceutical carrier is a liquid (solution, emulsion, or suspension) suitable for parenteral injection of the macrolide. In still other embodiments the pharmaceutical carrier is a solid or semi-solid (powder, sachet, tablet or capsule) dosage form suitable for oral ingestion that provides for immediate release of the macrolide into the gastric compartment. In other embodiments, the pharmaceutical carrier is a solid or semi-solid (powder, sachet, tablet or capsule) dosage form suitable for oral ingestion that provides for prolonged or controlled or sustained release of the macrolide into the gastric compartment. The methods and materials for achieving such formulations are known to those having ordinary skill in the art.

In more particular embodiments, the pharmaceutical carrier for the liquid oral dosage form containing the $\beta_2$-agonist is an aqueous solution of about 5 mM to about 200 mM buffer (acetate, citrate, phosphate, or succinate) adjusted to pH between 4 and 7 containing 3 to 6% of a sugar such as sorbitol, sucrose, dextrose, lactose, or mannitol plus about 0.01% to about 1% of an antimicrobial preservative such as sodium benzoate or potassium sorbate plus various flavoring and/or sweetening ingredients known to those in the art and capable of dissolving the $\beta_2$-agonist over the concentration range about 0.001 mg/mL to about 10 mg/mL. In still more particular embodiments, the pharmaceutical carrier for the oral solution dosage form containing the $\beta_2$-agonist is an aqueous solution of about 10 mM to about 30 mM citrate buffer adjusted to pH of between about 5.5 and about 6.5 containing about 4% to about 5% of mannitol plus about 0.05% to about 0.2% of potassium sorbate and various sweetening and/or flavoring ingredients. The methods and materials for achieving such formulations are known to those having ordinary skill in the art.

In still more particular embodiments, the pharmaceutical carrier for the parenteral injection dosage form containing the $\beta_2$-agonist is an aqueous solution of about 5 mM to about 200 mM buffer (acetate, citrate, phosphate, or succinate) adjusted to a pH of between about 4 and about 7 containing about 3% to about 6% of a sugar such as sorbitol, sucrose, dextrose, lactose, or mannitol and capable of dissolving the $\beta_2$-agonist over the concentration range about 0.001 mg/ML to about 10 mg/mL. In yet more particular embodiments, the pharmaceutical carrier for the parenteral solution dosage form containing the $\beta_2$-agonist is an aqueous solution of about 10 mM to about 30 mM citrate buffer adjusted to pH of between about 5.5 and about 6.5 containing about 4% to about 5% of mannitol. The methods and materials for achieving such formulations are known to those having ordinary skill in the art.

In more particular embodiments, the pharmaceutical carrier for the oral liquid dosage form containing the macrolide is an aqueous solution of about 5 mM to about 200 mM buffer (acetate, citrate, succinate, or phosphate) adjusted to a pH of between about 4 and about 7 containing about 3% to about 6% of a sugar such as sorbitol, sucrose, dextrose, lactose or mannitol plus about 0. 01% to about 1% of an antimicrobial preservative such as sodium benzoate or potassium sorbate plus various sweetening and/or flavoring ingredients known to those in the art and capable of dissolving the macrolide over the concentration range about 0.5 mg/mL to about 10 mg/mL. In still more particular embodiments, the pharmaceutical carrier for the liquid oral dosage form containing the macrolide is an aqueous solution of about 10 mM to about 30 mM citrate buffer adjusted to a pH of between about 5.5 and about 6.5 containing about 4% to about 5% of mannitol plus about 0.05% to about 0.2% of potassium sorbate plus a sweetening and/or flavoring ingredient. The methods and materials for achieving such formulations are known to those having ordinary skill in the art.

In more particular embodiments, the pharmaceutical carrier for the parenteral injection dosage form containing the macrolide is an aqueous solution of about 5 mM to about 200 mM buffer (acetate, citrate, succinate, phosphate) adjusted to a pH between about 4 and about 7 containing about 3% to about 6% of a sugar such as sorbitol, sucrose, dextrose, lactose, or mannitol and capable of dissolving the macrolide over the concentration range about 0.5 mg/mL to about 10 mg/mL. In still more particular embodiments, the pharmaceutical carrier for the parenteral solution dosage form containing the macrolide is an aqueous solution of about 10 mM to about 30 mM citrate buffer adjusted to a pH of between about 5.5 and about 6.5 containing about 4% to about 5% of mannitol. The methods and materials for achieving such formulations are known to those having ordinary skill in the art.

In still more particular embodiments, the pharmaceutical carrier for the solid oral dosage form containing the $\beta_2$-agonist is a microparticle of sucrose or microcrystalline cellulose (MCC) that has been coated with the $\beta_2$-agonist and a binder comprised of a polymer such as hydroxypropyl methylcellulose (HPMC) or polyvinylpyrrolidone (PVP) and overcoated with a polymer such as HPMC that affords essentially immediate release (total dissolution within about 60 minutes) of the $\beta_2$-agonist into the gastric contents. Immediate-release microparticles containing the $\beta_2$-agonist may be filled into capsules or pressed into tablets using methods known to those skilled in the art. Tablets and capsules containing the immediate-release $\beta_2$-agonist particles may also contain other inert, pharmaceutically acceptable excipients known to those skilled in the art, which may include (but are not necessarily limited to): lactose, starches, talc, or magnesium stearate. The methods and materials for achieving such formulations are known to those having ordinary skill in the art.

In another particular embodiment, the pharmaceutical carrier for the solid oral dosage form containing the $\beta_2$-agonist is a microparticle of sucrose or microcrystalline cellulose (MCC) that has been coated with the $\beta_2$-agonist and a binder comprised of a polymer such as hydroxypropyl methylcellulose (HPMC) or polyvinylpyrrolidone (PVP) and optionally overcoated with a suitable polymer that affords sustained, or prolonged, or controlled release of the $\beta_2$-agonist into the gastric contents. Controlled- or sustained- or prolonged-release microparticles containing the $\beta_2$-agonist may be filled into capsules or pressed into tablets using methods known to those skilled in the art. Tablets and capsules containing the sustained, or prolonged, or controlled-release $\beta_2$-agonist particles may also contain other inert, pharmaceutically acceptable excipients known to those skilled in the art, which may include (but are not necessarily limited to): lactose, starches, talc, or magnesium stearate. The methods and materials for achieving such formulations are known to those having ordinary skill in the art.

In another particular embodiment, the pharmaceutical carrier for the solid oral dosage form containing the macrolide is a microparticle containing about 50% to about 90% of the macrolide co-extruded with MCC plus a polymer binder such as HPMC that affords immediate release of the macrolide into the gastric contents. Immediate-release microparticles containing the macrolide may be filled into capsules or pressed into tablets using methods known to those skilled in the art. Tablets and capsules containing the sustained, or prolonged, or controlled-release $\beta_2$-agonist particles may also contain other inert, pharmaceutically acceptable excipients known to those skilled in the art, which may include (but are not necessarily limited to): lactose, starches, talc, or magnesium stearate The methods and materials for achieving such formulations are known to those having ordinary skill in the art.

In another particular embodiment, the pharmaceutical carrier for the solid oral dosage form containing the macrolide is a microparticle containing 50% to 90% of the macrolide co-extruded with MCC plus a suitable polymer binder such as such as HPMC and overcoated with a suitable polymer that affords sustained, or prolonged or controlled release of the macrolide into the gastric contents. Controlled- or sustained- or prolonged-release microparticles containing the macrolide may be filled into capsules or pressed into tablets using methods known to those skilled in the art. Tablets and capsules containing the sustained, or prolonged, or controlled-release $\beta_2$-agonist particles may also contain other inert, pharmaceutically acceptable excipients known to those skilled in the art, which may include (but are not necessarily limited to): lactose, starches, talc, or magnesium stearate. The methods and materials for achieving such formulations are known to those having ordinary skill in the art.

In some embodiments the $\beta_2$-agonist and the macrolide are combined into a single pharmaceutical carrier. Among the embodiments in which the $\beta_2$-agonist and the macrolide are administered in combination, the pharmaceutical carrier is a liquid (solution, syrup, suspension, or emulsion) suitable for oral ingestion or enteral administration using a naso-gastric tube. In other embodiments, the pharmaceutical carrier is a liquid (solution, suspension, or emulsion) suitable for parenteral injection of the $\beta_2$-agonist combined with the macrolide. In still other embodiments the pharmaceutical carrier is a solid or semi-solid (powder, sachet, tablet or capsule) dosage form suitable for oral ingestion that provides for immediate release of the $\beta_2$-agonist and the macrolide into the gastric compartment. In other embodiments, the pharmaceutical carrier is a solid or semi-solid (powder, sachet, tablet or capsule) dosage form suitable for oral ingestion that provides for prolonged or controlled or sustained release of the $\beta_2$-agonist and the macrolide into the gastric compartment. The methods and materials for achieving such formulations are known to those having ordinary skill in the art.

In more particular embodiments, the pharmaceutical carrier for the oral liquid dosage form containing both the $\beta_2$-agonist and the macrolide is an aqueous solution of about 5 mM to about 200 mM buffer (acetate, citrate, succinate, or phosphate) adjusted to pH of between about 4 and about 7 containing about 3% to about 6% of a sugar such as sorbitol, sucrose, dextrose, lactose, or mannitol plus about 0.0 1% to about 1% of an antimicrobial preservative such as sodium benzoate or potassium sorbate plus various flavoring and/or sweetening ingredients known to those skilled in the art and capable of dissolving the $\beta_2$-agonist over the concentration range about 0.001 mg/mL to about 10 mg/mL and also capable of dissolving the macrolide over the concentration range about 0.5 mg/mL to about 10 mg/mL. In still more particular embodiments, the pharmaceutical carrier for the oral solution dosage form containing both the $\beta_2$-agonist and the macrolide is an aqueous solution of about 10 mM to about 30 mM citrate buffer adjusted to pH of between about 5.5 and about 6.5 containing about 4% to about 5% of mannitol plus about 0.05% to about 0.2% of potassium sorbate and various sweetening and/or flavoring ingredients. The methods and materials for achieving such formulations are known to those having ordinary skill in the art.

In still more particular embodiments, the pharmaceutical carrier for the parenteral injection dosage form containing both the $\beta_2$-agonist and the macrolide is an aqueous solution of about 5 mM to about 200 mM buffer (acetate, citrate, succinate, or phosphate) adjusted to pH between about 4 and about 7 containing about 3% to about 6% of a sugar such as sorbitol, sucrose, dextrose, lactose or mannitol and capable of dissolving the $\beta_2$-agonist over the concentration range of between about 0.001 mg/mL to about 10 mg/mL and capable of dissolving the macrolide over the concentration range about 0.5 mg/mL to about 10 mg/mL. In yet more particular embodiments, the pharmaceutical carrier for the parenteral solution dosage form containing the $\beta_2$-agonist and the macrolide is an aqueous solution of about 10 mM to about 30 mM citrate buffer adjusted to pH of between about 5.5 and about 6.5 containing about 4% to about 5% of mannitol. The methods and materials for achieving such formulations are known to those having ordinary skill in the art.

In a more particular embodiment, the pharmaceutical carrier for the solid oral dosage form containing the both the $\beta_2$-agonist and the macrolide is a capsule or tablet containing immediate-release microparticles containing the $\beta_2$-agonist (as described above) and also containing immediate-release microparticles containing the macrolide (as described above). The proportions and amounts of immediate-release microparticles containing the $\beta_2$-agonist or the macrolide may be adjusted to give a desired dose of each drug in each capsule or tablet. Immediate-release microparticles may be filled into capsules or pressed into tablets using methods known to those skilled in the art. Tablets and capsules containing the immediate-release $\beta_2$-agonist particles may also contain other inert, pharmaceutically acceptable excipients known to those skilled in the art, which may include (but are not necessarily limited to): lactose, starches, talc, or magnesium stearate. The methods and materials for achieving such formulations are known to those having ordinary skill in the art.

In another more particular embodiment, the pharmaceutical carrier for the solid oral dosage form containing the both the $\beta_2$-agonist and the macrolide is a capsule or tablet containing controlled-or sustained- or prolonged-release microparticles containing the $\beta_2$-agonist (as described above) and also containing controlled-or sustained- or prolonged-release microparticles containing the macrolide (as described above). The proportions and amounts of controlled-or sustained- or prolonged-release microparticles containing the $\beta_2$-agonist or the macrolide may be adjusted to give a desired dose of each drug in each capsule or capsule. Sustained-, or prolonged- or controlled-release microparticles may be filled into capsules or pressed into tablets using methods known to those skilled in the art. Tablets and capsules containing the sustained-, or prolonged-, or controlled-particles may also contain other inert, pharmaceutically acceptable excipients known to those skilled in the art, which may include (but are not necessarily limited to): lactose, starches, talc, or magnesium stearate. The methods and materials for achieving such formulations are known to those having ordinary skill in the art.

In all of the embodiments describing pharmaceutical carriers, the dosage forms may be prepared using methods and techniques known to those skilled in the art. Representative methods and techniques may include (but are not necessarily limited): mixing (blending, stirring, sonicating, levigating, emulsifying, homogenizing), grinding, milling, heating/cooling, filtering, filling (liquid or powder) coating (spray or fluidized bed), drying (air, heat, spray, fluidized bed, or vacuum), extrusion, spheronization, and compression. The methods and materials for achieving such formulations are known to those having ordinary skill in the art.

Without wishing to be bound to any particular theory of action of the methods and compositions of the invention, it has been demonstrated that degradation of skeletal muscle proteins involves the ubiquitin-proteasome system. The ubiquitin-proteosome pathway, as an ATP-dependent regulatory system governing protein half-life, is involved in the regulation of the cell cycle, signal transmission, immune system response, apoptosis, and oncogenesis (Camps C, Iranzo V, et al., Support Care Cancer. 2006 Dec;14(12):1173-83. Epub 2006 Jul 4). This holds particularly for muscle wasting, also known as sarcopenia, which decreases the the quality of life of the geriatric population, increases morbidity, and decreases life expectancy (Inui A. "Feeding-related disorders in medicine, with special reference to cancer anorexia-cachexia syndrome", Rinsho Byori. 2006 October;54(10): 1044-51; Argiles JM, Busquets S, et al., Int J Biochem Cell Biol. 2005 May;37(5):1084-104. Epub 2004 Dec 30). Thus, in view of the biochemical and metabolic evidence, those having ordinary skill in the art will expect that the methods and compositions provided by the invention also can be used to treat sarcopenia and other disorders associated with dysregulation of the ubiquitin-proteasome system.

6 EXAMPLES

The following Examples are provided to illustrate certain aspects of the present invention and to aid those of skill in the art in the art in practicing the invention. These Examples are in no way to be considered to limit the scope of the invention in any manner.

6.1 Example 1

A Randomized, Double-blind, Pilot Study Comparing the Safety and Efficacy of the Invention with Placebo in the Prevention and Treatment of Cachexia in Patients with Advanced Cancer A study is performed to determine the impact of the formoterol fumarate-plus-roxithromycin combination on:
Eastern Cooperative Oncology Group (ECOG) performance status,
Body weight
Body composition determined by dual-energy X-ray absorptiometry (DEXA) and bioelectrical impedance analysis (BIA),
Quality of life (QoL) assessed using questionnaires,
Strength and endurance assessed by determinations of grip strength, grip strength fatigue, stair ascent/descent time, and 6-minute walk time, and
Serum levels of C-reactive Protein, IL6, and TNF and
Various safety parameters (e.g. blood chemistries, ECG, and clinical chemistries)

Study patients must be adults of either sex with advanced incurable non-small-cell lung cancer. Patients must have a life expectancy greater than 6 months per the investigator's initial clinical evaluation. Patients also are excluded if they show signs of renal or liver function outside of normal limits.

The study is a 18-week, two-arm, blinded, placebo-controlled trial with 30 patients per arm. The patients are grouped into two Cohorts:
Cohort 1: standard-of-care carboplatin doublet chemotherapy plus nutritional counseling plus roxithromycin plus formoterol fumarate;
Cohort 2: standard-of-care carboplatin doublet chemotherapy plus nutritional counseling plus roxithromycin placebo plus formoterol fumarate placebo;

Roxithromycin will be administered orally at 80 mg twice daily, and formoterol orally twice daily.

6.2 Example 2

A Randomized, Double-blind, Pilot Study Comparing the Safety and Efficacy of Roxithromycin alone, Formoterol alone, the Combination of Roxithromycin and Formoterol in the Prevention and Treatment of Cachexia in Patients with Advanced Cancer A study is performed to determine the impact of the formoterol fumarate-plus-roxithromycin combination on:
Eastern Cooperative Oncology Group (ECOG) performance status,
Body weight
Body composition determined by dual-energy X-ray absorptiometry (DEXA) and bioelectrical impedance analysis (BIA),
Quality of life (QoL) assessed using questionnaires,
Strength and endurance assessed by determinations of grip strength, grip strength fatigue, stair ascent/descent time, and 6-minute walk time, and
Serum levels of C-reactive Protein, IL6, and TNF and
Various safety parameters (e.g. blood chemistries, ECG, and clinical chemistries)

Study patients must be adults of either sex with advanced incurable non-small-cell lung cancer. Patients must have a life expectancy greater than 6 months per the investigator's initial clinical evaluation. Patients also are excluded if they show signs of renal or liver function outside of normal limits.

The study is a 18-week, four-arm, blinded, placebo-controlled trial with 30 patients per arm. The patients are grouped into four Cohorts:
Cohort 1: standard-of-care carboplatin doublet chemotherapy plus nutritional counseling plus roxithromycin plus formoterol fumarate;
Cohort 2: standard-of-care carboplatin doublet chemotherapy plus nutritional counseling plus roxithromycin plus formoterol fumarate placebo;
Cohort 3: standard-of-care carboplatin doublet chemotherapy plus nutritional counseling plus roxithromycin placebo plus formoterol fumarate;
Cohort 4: standard-of-care carboplatin doublet chemotherapy plus nutritional counseling plus roxithromycin placebo plus formoterol fumarate placebo;

Roxithromycin will be administered orally at 150 mg twice daily, and formoterol orally twice daily at its maximum tolerated dose.

6.3 Example 3

Muscle-Sparing Effects of Roxithromycin and Formoterol Fumarate in an Animal Model of Cancer Cachexia Following the method of Busquets et al (Busquets S, et al: Cancer Res 64:6725-31, 2004), female Wistar rats were inoculated (Day 0) intra-peritoneally (i.p.) with $2 \times 10^7$ cells/animal of Yoshida AH-130 ascites hepatoma (AH) cells. Control animals were inoculated with an equivalent amount of sterile saline solution. Beginning on Day 1, the animals were given once-daily doses of formoterol fumarate (i.p.), roxithromycin (i.p.), or matching inactive vehicle. The animals were sacrificed on Day 5. Upon sacrifice, wet weights of heart and gastrocnemius muscle were determined. Carcass (after gastrocnemius, heart, and ascites removal) weight was also determined upon sacrifice.

TABLE 1

Experimental Design for Rat AH130 Ascites Hepatoma Model of Cancer Cachexia

| Experiment # | Group # | Inoculum | Intraperitoneal Dose (mg/kg) | |
|---|---|---|---|---|
| | | | Formoterol Fumarate | Roxithromycin |
| 1 | 1 | AH* | 0 | 0 |
| 1 | 2 | Saline | 0 | 0 |
| 1 | 3 | AH* | 1 | 0 |
| 1 | 4 | AH* | 0 | 5 |
| 2 | 5 | AH* | 0 | 0 |
| 2 | 6 | Saline | 0 | 0 |

TABLE 1-continued

Experimental Design for Rat AH130 Ascites Hepatoma
Model of Cancer Cachexia

| | | | Intraperitoneal Dose (mg/kg) | |
|---|---|---|---|---|
| Experiment # | Group # | Inoculum | Formoterol Fumarate | Roxithromycin |
| 2 | 7 | AH* | 1 | 0 |
| 2 | 8 | AH* | 1 | 5 |
| 2 | 9 | Saline | 0 | 5 |
| 2 | 10 | Saline | 1 | 0 |
| 3 | 11 | AH* | 0 | 0 |
| 3 | 12 | Saline | 0 | 0 |
| 3 | 13 | AH* | 1 | 0 |
| 3 | 14 | AH* | 1 | 40 |
| 3 | 15 | Saline | 0 | 40 |
| 4 | 16 | AH* | 0 | 0 |
| 4 | 17 | Saline | 0 | 0 |
| 4 | 18 | AH* | 1 | 0 |
| 4 | 19 | AH* | 1 | 25 |
| 4 | 20 | AH* | 1 | 50 |
| 4 | 21 | AH* | 0 | 50 |

*$2 \times 10^7$ cells/animal of AH130 ascites hepatoma.

Table 2 shows the results of gravimetric determinations for Experiment 1. Table 3 shows the results of gravimetric determinations for Experiment 2. Table 4 shows the results of gravimetric determinations for Experiment 3. Table 5 shows the results of gravimetric determinations for Experiment 4. Below, the treatment groups are designated by the following conventions:

Treatment Group=Inoculation Type/Vehicle, or Treatment Group=Inoculation Type/F(x)R(y) where, Inoculation Type is either AH or Saline, F is formoterol fumarate, R is roxithromycin, and the parenthetical values are formoterol fumarate and roxithromycin doses (i.p. in mg/kg).

TABLE 2

Gravimetric Data for Rat AH Experiment 1

| Group | Inoculum | Dose (mg/kg)* F | R | N** | Heart Weights, g*** Mean | SEM | Gastrocnemius Weights, g*** Mean | SEM | Carcass Weights, g*** Mean | SEM |
|---|---|---|---|---|---|---|---|---|---|---|
| 1 | AH | 0 | 0 | 7 | 0.320 | 0.008 | 0.503 | 0.005 | 93.96 | 0.70 |
| 2 | Saline | 0 | 0 | 7 | 0.359 | 0.010 | 0.588 | 0.007 | 96.26 | 0.75 |
| 3 | AH | 1 | 0 | 7 | 0.337 | 0.009 | 0.551 | 0.012 | 95.35 | 0.86 |
| 4 | AH | 0 | 5 | 9 | 0.320 | 0.009 | 0.493 | 0.004 | 94.35 | 0.71 |

*F = formoterol fumarate, R = roxithromycin
**Number of evaluated animals. Animals that accumulated <1 mL of ascites were not considered in the analysis
***Sample weights normalized to 100 g of Day 5 Total Body Weight

TABLE 3

Gravimetric Data for Rat AH130 Experiment 2

| Group | Inoculum | Dose (mg/kg)* F | R | N | Heart Weights, g** Mean | SEM | Gastrocnemius Weights, g** Mean | SEM | Carcass Weights, g** Mean | SEM |
|---|---|---|---|---|---|---|---|---|---|---|
| 5 | AH | 0 | 0 | 10 | 0.349 | 0.0060 | 0.487 | 0.0090 | 92.5 | 0.91 |
| 6 | Saline | 0 | 0 | 10 | 0.398 | 0.0080 | 0.565 | 0.0100 | 98.2 | 0.27 |
| 7 | AH | 1 | 0 | 10 | 0.348 | 0.0090 | 0.499 | 0.0050 | 89.7 | 0.53 |
| 8 | AH | 1 | 5 | 10 | 0.358 | 0.0100 | 0.514 | 0.0090 | 90.7 | 0.83 |
| 9 | Saline | 0 | 5 | 10 | 0.390 | 0.0110 | 0.575 | 0.0070 | 97.6 | 0.48 |
| 10 | Saline | 1 | 0 | 7 | 0.410 | 0.0100 | 0.613 | 0.0080 | 97.6 | 0.26 |

*F = formoterol fumarate, R = roxithromycin
**Sample weight normalized to 100 g of Day 5 Total Body Weight

TABLE 4

Gravimetric Data for Rat AH Experiment 3

| Group | Inoculum | Dose (mg/kg)* F | R | N | Heart Weights, g** Mean | SEM | Gastrocnemius Weights, g** Mean | SEM | Carcass Weights, g** Mean | SEM |
|---|---|---|---|---|---|---|---|---|---|---|
| 11 | AH | 0 | 0 | 10 | 0.341 | 0.0070 | 0.431 | 0.0040 | 93.6 | 0.52 |
| 12 | Saline | 0 | 0 | 10 | 0.417 | 0.0120 | 0.536 | 0.0060 | 95.2 | 0.83 |
| 13 | AH | 1 | 0 | 10 | 0.376 | 0.0140 | 0.489 | 0.0090 | 93.1 | 0.69 |
| 14 | AH | 1 | 40 | 10 | 0.350 | 0.0360 | 0.528 | 0.0100 | 95.9 | 0.58 |
| 15 | Saline | 0 | 40 | 10 | 0.400 | 0.0070 | 0.529 | 0.0080 | 96.5 | 0.52 |

*F = formoterol fumarate, R = roxithromycin
**Sample weight normalized to 100 g of Day 5 Total Body Weight

TABLE 5

Gravimetric Data for Rat AH Experiment 4

| Group | Inoculum | Dose (mg/kg)* F | R | N | Heart** Mean | SEM | Gastrocnemius** Mean | SEM | Carcass** Mean | SEM |
|---|---|---|---|---|---|---|---|---|---|---|
| 16 | AH | 0 | 0 | 10 | 0.323 | 0.0080 | 0.453 | 0.0051 | 97.2 | 0.59 |
| 17 | Saline | 0 | 0 | 10 | 0.405 | 0.0069 | 0.556 | 0.0080 | 96.5 | 0.84 |
| 18 | AH | 1 | 0 | 10 | 0.367 | 0.0160 | 0.502 | 0.0120 | 97.8 | 0.35 |
| 19 | AH | 1 | 25 | 10 | 0.344 | 0.0085 | 0.477 | 0.0080 | 97.1 | 0.45 |
| 20 | AH | 1 | 50 | 10 | 0.373 | 0.0106 | 0.520 | 0.0097 | 97.4 | 0.25 |
| 21 | AH | 0 | 50 | 10 | 0.338 | 0.0130 | 0.500 | 0.0092 | 94.1 | 0.68 |

*F = formoterol fumarate, R = roxithromycin
**Sample weight normalized to 100 g of Day 5 Total Body Weight In Experiment 1 (see Table 2), gastrocnemius muscle loss was significantly greater for the AH/vehicle group than for the saline/vehicle group, indicating the highly cachectic nature of the ascites hepatoma. Animals in the AH/F(1)R(0) group lost significantly less gastrocnemius muscle than animals in the AH/vehicle group. Animals in the AH/F(0)R(5) group lost approximately the same amount of gastrocnemius muscle as animals in the AH/vehicle group. The trends observed for gastrocnemius muscle weight changes in various treatment groups roughly paralleled those observed for heart and carcass weights (see Tables 3-6), indicating that the effects of AH inoculation and treatments were general and not limited to gastrocnemius muscle.

The effects of AH and formoterol fumarate treatment on gastrocnemius muscle weights in Experiment 2 were similar to the effects seen in Experiment 1. In Experiment 2, gastrocnemius weights for animals in the AH/F(1)R(5) group were not significantly different from muscle weights for animals in the AH/F(1)R(0) group. Rats in the Saline/F(0)R(5) and Saline/F(1)R(0) groups had approximately the same gastrocnemius muscle weights as rats in the Saline/vehicle group.

The effects of AH and formoterol fumarate treatment on gastrocnemius muscle weights in Experiment 3 were similar to the effects seen in Experiment 1. In Experiment 3, rats in the AH/F(1)R(40) group had much greater gastrocnemius muscle weights than rats in the AH/F(1)R(0) group. Surprisingly, for animals in the AH/F(1)R(40) group, gastrocnemius weights were not significantly different than muscle weights for animals in the Saline/vehicle control group. Gastrocnemius muscle weights were also not different in the Saline/F (O)R(40) group compared with the Saline/vehicle control group.

The effects of AH and formoterol fumarate treatment on gastrocnemius muscle weights in Experiment 4 were similar to the effects seen in Experiment 1. In Experiment 4, gastrocnemius muscle weights for rats in the AH/F(1)R(25) group were not significantly different than muscle weights for rats in the AH/F(1)R(0) group. For animals in the AH/F(1)R(50) group, gastrocnemius weights were larger than muscle weights for animals in the AH/F(1)R(0) group. The animals in the AH/F(0)R(50) group demonstrated significantly larger gastrocnemius muscle weights than animals in the AH/vehicle group. Also for the rats in the AH/F(0)R(50) group, gastrocnemius weights were essentially identical to muscle weights for rats in the AH/F(1)R(0) group and slightly less than muscle weights for rats in the AH/F(1)R(50) group.

FIG. 1 illustrates the effects of 40 and 50 mg/kg roxithromycin (with and without 1 mg/kg formoterol fumarate) on gastrocnemius muscle in AH-inoculated rats.

In summary, the scientific literature establishes that muscle loss is very rapid in the rat ascites hepatoma cancer cachexia model, and that formoterol fumarate administered by intraperitoneal injection antagonizes cancer cachexia. Surprisingly, we have discovered that roxithromycin also prevents muscle wasting associated with the AH rat model. Indeed, we have shown that roxithromycin administered alone was effective as formoterol fumarate alone in preventing AH-induced gastrocnemius muscle loss. The muscle-sparing effect of roxithromycin combined with formoterol fumarate was greater than the effect of either drug given individually at the same doses. These data show that roxithromycin and formoterol fumarate work in combination to antagonize cachexia and increase protein synthesis. Without being bound to any theory of action, the data are consistent with a mechanism of action in which formoterol fumarate prevents cachexia by reducing proteolysis via the ubiquitin-proteasome pathway, and roxithromycin's mechanism of action relates to suppressing pro-inflammatory cytokines such as IL-6 and TNF. Thus, the formoterol fumarate plus roxithromycin combination offers the promise of an effective, truly multimodal therapy for patients at risk of or suffering from cachexia and anorexia.

6.4 Example 4

Effects of pH and Buffer Strength on Aqueous Solubility of Roxithromycin

An amount of roxithromycin equivalent to 10 mg/mL was added to various solutions and agitated for 24 hours at 25° C. The solutions were syringe-filtered and analyzed by HPLC for [roxithromycin]. Roxithromycin Potency was assayed by a reverse-phase HPLC method that meets the requirements of the European Pharmacopeia (EP) Monograph for roxithromycin. Solution pH values were determined per USP <791> and solution osmolality values were determined per USP <785>. Aqueous solubility limits were determined for roxithromycin as a function of buffer type (phosphate versus citrate), buffer concentration, pH, and added co-solvent (ethanol).

Table 6 shows the results for roxithromycin solubility in phosphate buffers with no added ethanol. Table 7, Table 8, and Table 9 show the results for roxithromycin solubility in phosphate buffers (10 mM, 20 mM, and 50 mM, respectively) with ethanol co-solvent added at 0, 5, and 10%. Together, the tables show that roxithromycin solubility increases with decreasing pH, increasing phosphate concentration, and increasing % ethanol over the ranges studied.

TABLE 6

Roxithromycin Solubility at 25° C. As A Function of pH in Phosphate Buffers Without Added Ethanol Co-solvent

| | [Roxithromycin] mg/mL at [Phosphate] = (mM) | | |
|---|---|---|---|
| pH | 10 | 20 | 50 |
| 5 | 3.2 | 5.2 | 7.2 |
| 6 | 2.8 | 4.2 | 6.7 |
| 7 | 1.4 | 1.3 | 2.0 |

TABLE 7

Roxithromycin Solubility at 25° C. As A Function of pH in 10 mM Phosphate Buffers With Added Ethanol Co-solvent

| | [Roxithromycin] mg/mL in 10 mM Phosphate and Ethanol (%) = | | |
|---|---|---|---|
| pH | 0 | 5 | 10 |
| 5 | 3.2 | 3.5 | 3.8 |
| 6 | 2.8 | 4.1 | 3.9 |
| 7 | 1.4 | 1.8 | 1.7 |

TABLE 8

Roxithromycin Solubility at 25° C. As A Function of pH in 20 mM Phosphate Buffers With Added Ethanol Co-solvent

| | [Roxithromycin] mg/mL in 20 mM Phosphate and Ethanol (%) = | | |
|---|---|---|---|
| pH | 0 | 5 | 10 |
| 5 | 5.2 | 5.5 | 6.0 |
| 6 | 4.2 | 4.6 | 5.0 |
| 7 | 1.3 | 1.7 | 2.1 |

TABLE 9

Roxithromycin Solubility at 25 ° C. As A Function of pH in 50 mM Phosphate Buffers With Added Ethanol Co-solvent

| | [Roxithromycin] mg/mL in 50 mM Phosphate and Ethanol (%) = | | |
|---|---|---|---|
| pH | 0 | 5 | 10 |
| 5 | 7.2 | 8.3 | 9.2 |
| 6 | 6.7 | 8.1 | 9.3 |
| 7 | 2.0 | 2.3 | 3.1 |

Table 10 summarizes the data for roxithromycin solubility and solution osmolality in citrate buffers as a function of pH, and citrate concentration. The table shows that osmolality increases, with increasing [citrate] and increasing pH over the ranges studies. Roxithromycin solubility decreases with increasing pH, as noted above for studies with phosphate buffer. For citrate buffer solutions, roxithromycin solubility shows a complex dependence on citrate concentration.

TABLE 10

Roxithromycin Solubility and Solution Osmolality At 25° C. As A Function of pH and [Citrate]

| [Citrate], mM | pH | Solution Osmolaltiy, mOsm/kG | [Roxithromycin], mg/mL |
|---|---|---|---|
| 200 | 4 | 366 | 2.74 |
| 200 | 5 | 462 | 1.90 |
| 200 | 6 | 521 | 1.72 |
| 200 | 7 | 532 | 1.25 |
| 100 | 4 | 203 | 1.89 |
| 100 | 5 | 243 | 2.77 |
| 100 | 6 | 260 | 2.30 |
| 100 | 7 | 271 | 1.23 |
| 50 | 4 | 110 | 4.61 |
| 50 | 5 | 124 | 3.57 |
| 50 | 6 | 139 | 2.76 |
| 50 | 7 | 138 | 0.98 |
| 20 | 4 | 43 | 4.13 |
| 20 | 5 | 47 | 3.54 |
| 20 | 6 | 57 | 2.45 |
| 20 | 7 | 60 | 0.50 |

In summary, this example demonstrates that decreasing pH (range 4 to 7), increasing concentration of ethanol co-solvent (range 0 to 10%), and decreasing citrate buffer concentration (range 20 to 200 mM) increase roxithromycin solubility.

6.5 Example 5

Effects of pH and Buffer Strength on Aqueous Stability of Roxithromycin

Roxithromycin stability was determined for 2 mg/mL [roxithromycin] at 5, 25, and 40° C. as a function of pH and buffer (citrate) concentration. Roxithromycin %Purity was determined by area normalization using a reverse-phase HPLC method that meets the requirements of the EP Monograph. Solution pH values were determined per USP <791>.

Table 11 shows the %Purity values versus storage interval (in months) for roxithromycin 2 mg/mL solutions maintained at 40° C. Table 12 and Table 13 show the %Purity data for roxithromycin solutions maintained at 25° C. and 5° C., respectively.

TABLE 11

Roxithromycin (2 mg/mL) % Purity Values versus Storage Interval at 40° C. in Citrate Buffer As A Function of [Citrate] and pH

| Buffer | Roxithromycin % Purity By Area Normalization at Time (mo) = | | | | | | |
|---|---|---|---|---|---|---|---|
| | 0 | 0.3 | 0.5 | 0.9 | 1.5 | 2.6 | 5.3 |
| pH 5, 100 mM | 90 | 60 | 46 | 31 | 14 | 4 | |
| pH 6, 100 mM | 98 | 85 | 77 | 72 | 66 | 58 | 48 |
| pH 4, 50 mM | 78 | 15 | 3 | 1 | | | |
| pH 5, 50 mM | 92 | 66 | 55 | 44 | 28 | 13 | 3 |
| pH 6, 50 mM | 98 | 89 | 82 | 77 | 71 | 65 | 61 |
| pH 4, 20 mM | 81 | 27 | 10 | 2 | | | |
| pH 5, 20 mM | 96 | 74 | 66 | 60 | 50 | 36 | 21 |
| pH 6, 20 mM | 98 | 95 | 92 | 89 | 84 | 79 | 76 |

TABLE 12

Roxithromycin (2 mg/mL) % Purity Values versus Storage Interval at 25° C. in Citrate Buffer As A Function of [Citrate] and pH

| Buffer | Roxithromycin % Purity By Area Normalization at Time (mo) = | | | | | | | |
|---|---|---|---|---|---|---|---|---|
| | 0 | 0.3 | 0.5 | 0.9 | 1.5 | 2.6 | 5.3 | 7.3 |
| pH 5, 100 mM | 90 | 79 | 76 | 75 | 73 | 67 | 60 | 50 |
| pH 6, 100 mM | 98 | 94 | 92 | 89 | 85 | 81 | 78 | 76 |
| pH 4, 50 mM | 78 | 71 | 65 | 59 | 47 | 33 | 15 | 6 |
| pH 5, 50 mM | 92 | 82 | 78 | 77 | 74 | 71 | 67 | 59 |
| pH 6, 50 mM | 98 | 96 | 94 | 92 | 89 | 85 | 81 | 78 |
| pH 4, 20 mM | 81 | 74 | 70 | 65 | 56 | 48 | 28 | 15 |
| pH 5, 20 mM | 96 | 88 | 84 | 80 | 77 | 75 | 75 | 71 |
| pH 6, 20 mM | 98 | 97 | 96 | 96 | 94 | 92 | 90 | 87 |

TABLE 13

Roxithromycin (2 mg/mL) % Purity Values versus Storage Interval at 5° C. in Citrate Buffer As A Function of [Citrate] and pH

| Buffer | Roxithromycin % Purity By Area Normalization at Time (mo) = | | | | | | | |
|---|---|---|---|---|---|---|---|---|
| | 0 | 0.3 | 0.5 | 0.9 | 1.5 | 2.6 | 5.3 | 7.3 |
| pH 5, 100 mM | 90 | 85 | 83 | 81 | 79 | 78 | 76 | 76 |
| pH 6, 100 mM | 90 | 96 | 95 | 95 | 93 | 90 | 86 | 84 |
| pH 4, 50 mM | 98 | 76 | 76 | 75 | 73 | 71 | 64 | 60 |
| pH 5, 50 mM | 78 | 88 | 85 | 84 | 81 | 79 | 78 | 77 |
| pH 6, 50 mM | 92 | 97 | 96 | 96 | 95 | 93 | 90 | 87 |
| pH 4, 20 mM | 98 | 78 | 77 | 77 | 75 | 74 | 69 | 67 |
| pH 5, 20 mM | 81 | 93 | 91 | 89 | 85 | 82 | 80 | 79 |
| pH 6, 20 mM | 96 | 98 | 97 | 97 | 97 | 96 | 96 | 94 |

In summary, this example demonstrates that increasing pH (range 4 to 6) and decreasing citrate concentration (range 20 mM to 100 mM) increase roxithromycin stability. An aqueous formulation containing 2 mg/mL roxithromycin, and 20 mM citrate buffer at pH 6 showed satisfactory and stability.

6.6 Example 6

Effects of pH and Buffer Strength on Aqueous Solubility of Formoterol Fumarate

An amount of formoterol fumarate equivalent to 10 mg/mL was added to various solutions. The solutions were agitated for 24 hours at 25° C., syringe filtered, and analyzed for formoterol fumarate concentration by the reverse-phase HPLC method in the European Pharmacopeial Monograph for Formoterol Fumarate Dihydrate. Aqueous solubility limits were determined for formoterol fumarate as a function of citrate buffer concentration (20 to 200 mM), and pH (4 to 7).

Table 10 summarizes the data for formoterol fumarate solubility and solution osmolality in citrate buffers as a function of pH, and citrate concentration. The table shows that osmolality increases with increasing citrate concentration and increasing pH over the ranges studies. Formoterol fumarate solubility decreases with increasing pH. For citrate buffer solutions, formoterol fumarate solubility shows a complex dependence on citrate concentration. These data demonstrate that formoterol fumarate solubility is relatively insensitive to pH and citrate concentration in the range pH 5 to 7. Formoterol fumarate solubility is somewhat higher at a pH of 4 than at pH>5.

Table 14

Formoterol Fumarate Solubility and Solution Osmolality At 25° C.
As A Function of pH and [Citrate]

| [Citrate], mM | pH | Formoterol Filtrate mOsm/kG | Formoterol, mg/mL** |
|---|---|---|---|
| 200 | 4 | 392 | 3.69 |
| 200 | 5 | 473 | 2.90 |
| 200 | 6 | 527 | 2.72 |
| 200 | 7 | 543 | 2.84 |
| 100 | 4 | 205 | 3.01 |
| 100 | 5 | 249 | 2.69 |
| 100 | 6 | 275 | 2.87 |
| 100 | 7 | 278 | 2.60 |
| 50 | 4 | 113 | 3.69 |
| 50 | 5 | 130 | 2.77 |
| 50 | 6 | 140 | 2.78 |
| 50 | 7 | 146 | 2.92 |
| 20 | 4 | 49 | 2.71 |
| 20 | 5 | 56 | 2.35 |
| 20 | 6 | 60 | 2.47 |
| 20 | 7 | 66 | 2.33 |

Ideally, a formoterol fumarate oral solution dosage form will support formoterol fumarate concentrations- of approximately 0.001 to 0.005 mg/mL, so that a patient dose between 0.08 and 0.32-mg (anticipated dose needed for anti-cachectic activity) will require a dosing volume of approximately 75 mL. The solubility screening studies described in this example show that formoterol fumarate is soluble to >1 mg/mL in citrate buffer concentrations between 20 and 200 mM at pH 4 to pH 7.

6.7 Example 7

Stability of 0.020 mg/mL Formoterol Fumarate in 20 mM citrate buffer (pH 5.5) with 4.5% mannitol and 0.1% potassium sorbate According to Banerjee et al. (U.S. Pat. No. 6,667,344), formoterol fumarate stability over the range pH=3 to pH=7 is optimal at approximately pH 5, Banerjee et al. state in the referenced patent that "The rate constant at 60° C. at a pH of 3, 4, 5 and 7 is approximately 0.62, 0.11, 0.044 and 0.55 day$^1$, respectively. Therefore, the decomposition of formoterol in aqueous solution at 60° C. at a buffer concentration of 5 mM and an ionic strength of 0.05 is slowest at a pH of about 5.0. The estimated shelf-life of formoterol in the compositions provided herein is about 6.2 years at 5° C. and about 7.5 months at 25° C."

To demonstrate the stability of formoterol fumarate in a vehicle suitable for use as an oral dosing solution, formoterol fumarate was made to 0.020 mg/mL in an aqueous solution containing 20 mM citrate buffer (pH 5.5), 4.5% mannitol, and 0.1% potassium sorbate. Samples of this formulation were maintained at 5, 25, and 40° C. At timed intervals, aliquots of these samples were withdrawn and [formoterol fumarate] potency was determined by a reverse-phase HPLC method reported in the literature by Akapo et al. (Akapo, et al.: J Pharm Biomed Anal 33:935-45, 2003). Solution pH values were determined per USP<791> and solution osmolality values were determined per USP<785>.

Table 15 shows the osmolality data and demonstrates no change in osmolality for the conditions studied. Table 16 summarizes the pH data, and demonstrates no significant changes for the conditions investigated. Table 17 summarizes the formoterol fumarate potency data for solutions maintained for timed intervals at 5, 25, and 40° C. Formoterol fumarate potency loss at the 3-mo timepoint was negligible at 5° C. and approximately 3% at 25° C. At the 1.5-mo timepoint, formoterol fumarate potency loss was approximately 15% at 40° C.

TABLE 15

Osmolality Results for 0.020 mg/mL Formoterol Fumarate at pH 5.5 in 20 mM Citrate Buffer plus 4.5% Mannitol and 0.1% Potassium Sorbate

| | Osmolality (mOsm) at Temperature = | | |
|---|---|---|---|
| Timepoint, Mo | 5° C. | 25° C. | 40° C. |
| 0.5 | N/A | 332 | 331 |
| 1.5 | 331 | 332 | 333 |
| 3.0 | 338 | 336 | N/A |

TABLE 16 pH Results for 0.020 mg/mL Formoterol Fumarate at pH 5.5 in 20 mM Citrate Buffer plus 4.5% Mannitol and 0.1% Potassium Sorbate

| | Solution pH at Temperature = | | |
|---|---|---|---|
| Timepoint, mo | 5° C. | 25° C. | 40° C. |
| 0 | 5.54 | N/A | N/A |
| 0.5 | N/A | 5.53 | 5.53 |
| 1.5 | 5.59 | 5.54 | 5.59 |
| 3.0 | 5.57 | 5.56 | N/A |

TABLE 17

Formoterol Fumarate Potency For pH 5.5, 20 mM Citrate Solutions Containing 4.5% Mannitol and 0.1% Potassium Sorbate[a,b]

| | [Formoterol Fumarate], mg/mL at Time (mo) = | | | | |
|---|---|---|---|---|---|
| Temp, ° C. | 0 | 0.25 | 0.5 | 1.5 | 3 |
| 40 | 0.0206 | | 0.0189 | 0.0175 | |
| 40 | 0.0207 | | 0.0190 | 0.0175 | |
| 25 | 0.0206 | 0.0203 | 0.0196 | 0.0199 | 0.0200 |
| 25 | 0.0207 | 0.0204 | 0.0198 | 0.0200 | 0.0200 |
| 5 | 0.0206 | | | 0.0202 | 0.0208 |
| 5 | 0.0207 | | | 0.0203 | 0.0209 |

[a]Results are shown as average of two injections for duplicate samples
[b]Blank cells represents data that were not determined This example shows that through the 3-mo timepoint, formoterol fumarate potency loss was negligible ° C. and approximately 3% at 25° C. Through the 1.5-mo timepoint, formoterol fumarate potency loss was approximately 15% at 40° C.

6.8 Example 8

Stability of Formoterol Fumarate and Roxithromycin Co-formulated in pH 6, 20 mM citrate buffer plus 4.5% mannitol and 0.1% potassium Sorbate.

To demonstrate the stability of formoterol fumarate combined with roxithromycin in a vehicle suitable for use as an oral dosing solution, formoterol fumarate was made to 0.005 mg/mL and roxithromycin was made to 2.0 mg/mL in an aqueous solution containing 20 mM citrate buffer (pH 6.0), 4.5% manntol, and 0.1% potassium sorbate. Samples of this formulation were maintained at 5, 25, and 40° C. and tested after 0, 2, and 4 weeks for potency of formoterol fumarate and potency of roxithromycin. Formoterol fumarate potency was determined by a reverse-phase HPLC method reported in the literature by Akapo et al. (Akapo, et al.: J Pharm Biomed Anal 33:935-45, 2003). Roxithromycin Potency was assayed by a reverse-phase HPLC method that meets the requirements of the European Pharmacopeia (EP) Monograph for roxithromycin. Table 18 shows the formoterol fumarate potency data, and Table 19 shows the roxithromycin potency data. Through the 4-week timepoint, the stability data demonstrate no evidence of increased degradation for the combination formulation compared with similar data for formoterol fumarate alone (Example 7) or roxithromycin alone (Example 5).

TABLE 18

Formoterol Fumarate Potency (μg/mL) Values Through t = 4-Week Timepoint at 5, 25, and 40° C.

| Time | Formoterol Potency (μg/mL) at Temp, ° C. = | | |
|---|---|---|---|
| | 5 | 25 | 40 |
| 0 | 4.73 | 4.73 | 4.73 |
| 2 | not tested | 4.91 | 4.76 |
| 4 | 4.92 | 4.73 | 3.95 |

TABLE 19

Roxithromycin Potency (mg/mL) Values Through t = 4-Week Timepoint at 5, 25, and 40° C.

| Time | Roxithromycin Potency (mg/mL) at Temp, ° C. = | | |
|---|---|---|---|
| | 5 | 25 | 40 |
| 0 | 1.92 | 1.92 | 1.92 |
| 2 | | 1.74 | 1.61 |
| 4 | 1.92 | 1.71 | 1.47 |

6.9 Example 9

Effects of Various Co-solvents and Excipients on Aqueous Solubility of Megestrol Acetate Examples 4-8, show that a vehicle containing about 20 mM citrate plus 4.5% mannitol at pH between 5 and 6 is potentially suitable as a liquid oral dosage form for a combination of roxithromycin at 2 mg/mL and formoterol fumarate at approximately about 5 μg/mL to about 50 μg/mL. Because megestrol acetate might enhance the effectiveness of a roxithromycin:formoterol combination for prevention and treatment of cancer cachexia, there is potential value (with respect to patient compliance) in developing a 3-drug combination oral solution formulation containing megestrol acetate plus roxithromycin and formoterol. Marketed oral dosage forms of megestrol acetate include 40 mg tablets, an 800 mg/20 mL suspension, and a 625 mg/5mL oral suspension.

Stability data shown in Examples 5 and 7 indicate that a pH 5 to 6, 20 mM citrate buffer formulatio containing roxithromycin and formoterol fumarate would require refrigerated temperatures for long term storage, and room temperature storage for short-term patient use. A 150-mg dose of roxithromycin could be administered via a 75-mL dosing volume of the 2 mg/mL solution. Target boundary conditions for a 3-drug combination oral solution, therefore include:

0.5 to 4 mg/mL solubility for megestrol acetate (=300 mg per 600- to 75-mL dosing volume to be given bid, as required for roxithromycin)

pH 5 to 6 (required for roxithromycin and formoterol storage stability)

refrigerated storage (required for roxithromycin and formoterol storage stability)

chemical and physical compatibility with roxithromycin and formoterol

Because the intrinsic aqueous solubility of megestrol acetate is 2 μg/mL (FDA-approved package insert for Bristol Meyers Squibb Megestrol Acetate 40 mg tablets), developing a solution formulation suitable for oral dosing will require the use of co-solvents, surfactants, complexing agents, and/or combinations of these inactive ingredients.

Solvents and cyclodextrin complex-forming agents were added in various proportions to an aqueous solution of pH 5.5, 20 mM citrate buffer containing 4.5% mannitol. Excess (10 mg/mL) megestrol acetate was added to each test solution and undissolved megestrol acetate was removed by filtration after agitation for 24 h at 5 ° C. The [megestrol acetate] in each test solution was determined by an adaptation of the reverse-phase HPLC method described by: Burana-Osot J, et al.: J Pharm Biomed Anal 40:1068-72, 2006. The results of this investigation of megestrol acetate aqueous solubility limits demonstrated that 12 test solutions increase megestrol aqueous solubility to>0.5 mg/mL. The 12 test solutions (and the corresponding megestrol acetate solubility limits) are:

80:20 polyethylene glycol (PEG) 600 average molecular weight: Buffer (0.6 mg/mL)

80:20 PEG 400 average molecular weight: Buffer (0.8 mg/mL)

Tocopheryl Polyethyleneglycol 1000 Succinate, 10% in 55:20:25 Propylene glycol:PEG 400: Buffer (0.8 mg/mL)

20% Beta-cyclodextrin (0.8 mg/mL)

30% Beta-cyclodextrin (1.3 mg/mL)

3% Heptakis (2,6-di-O-methyl) beta-cyclodextrin (1.1 mg/mL)

10% Heptakis (2,6-di-O-methyl) beta-cyclodextrin (3.3 mg/mL)

3% Sulfobutylether beta-cyclodextrin, Sodium Salt (0.8 mg/mL)

10% Gamma-cyclodextrin (0.6 mg/mL)

3% 2-Hydroxypropyl beta-cyclodextrin Degree of Substitution 4.3 (0.6 mg/mL)

10% 2-Hydroxypropyl beta-cyclodextrin Degree of Substitution 4.3 (1.2 mg/mL), and 10% Carboxymethylated beta-cyclodextrin Degree of Substitution 3 (0.7 mg/mL)

In the list above, most of the solutions contributing to high megestrol acetate solubility contain cyclodextrin complex-forming agents. It is not unexpected that cyclodextrins increase megestrol acetate aqueous solubility insofar as the literature contains multiple references to using cyclodextrins for increasing the solubility of drugs in general (Strickley R G: Pharm Res 21:201-30, 2004, Albers E, and Muller B W: Crit Rev Ther Drug Carrier Syst 12:311-37, 1995), and steroid hormones (Albers E, and Muller B W: J Pharm Sci 81:756-61, 1992, Nandi I, et al: AAPS PharmSciTech 4:E1, 2003, Cserhati T, and Forgacs E: J Pharm Biomed Anal 18:179-85, 1998, Albers E, and Muller B W: J Pharm Sci 81:756-61, 1992, Pitha, J., U.S. Pat. No 4,727,064, February 1988) and, macrolide antibiotics (Shastri, V., et al. U.S. Pat. No 6,699,505, Mar. 2004, Salem: Int J Pharm 250:403-14, 2003) in particular. Similarly, the solubility enhancement afforded to megestrol acetate by PEG 400, and PEG 600 co-solvents is consistent with literature observations (Millard J, et al.: Int J Pharm 245:153-66, 2002, Li P, et al.: J Pharm Sci 88:1107-11, 1999). Also, the solubility enhancement afforded to megestrol acetate by tocopheryl polyethyleneglycol succinate is consistent with literature observations (Roy et al, U.S. Pat. No 6,730,679, 4 May 2004, Yu, et al., Pharm. Res., 16:1812-1817, 1999). It is surprising, however, that any of the 12 solutions listed above could also be used to prepare liquid oral dosage forms containing megestrol acetate, plus the combination of formoterol fumarate and roxithromycin. As shown in Examples 4-8, roxithromycin and formoterol fumarate can be suitably formulated in 20 mM citrate buffer plus 4.5% mannitol at pH 5 to 6. Any of the 11 solutions listed in the above example would therefore be suitable for a three-drug combination liquid oral dosage form containing 2 mg/mL roxithromycin, 0.005 mg/mL formoterol and >0.5 mg/mL megestrol acetate. Such a formulation with appropriate preservative and flavoring agents added would have practical utility for treating patients suffering from cachexia.

6.10 Example 10

Roxithromycin and Formoterol Fumarate Multiparticulate Solid Oral Dosage Forms

Treatment and prevention of cachexia and anorexia in humans will probably require a 300 mg/day roxithromycin dose and a 160 µg/day formoterol fumarate dose. Although patients could be successfully dosed twice daily with roxithromycin and formoterol fumarate co-administered as separate solid oral dosage forms, there is an obvious patient compliance advantage to having both active pharmaceutical ingredients combined into a single solid oral dosage form. Another obvious advantage from a compliance perspective would be to have both active pharmaceutical ingredients in a single solid oral dosage form with slow-release properties such that the combination could be administered once daily.

Factors driving the design of a suitable combination solid oral dosage form for roxithromycin and formoterol fumarate include:
 widely different doses for the two active ingredients,
 environmental health and safety concerns regarding handling the very potent formoterol fumarate active pharmaceutical ingredient in dispersed form,
 flexibility in changing the strength of roxithromycin and formoterol fumarate dosage forms throughout clinical development,
 size of the combined solid oral dosage form,
 taste masking of roxithromycin,
 potential chemical interactions between roxithromycin and formoterol fumarate, and
 flexibility in choosing between immediate-release versus slow-release dosage forms.

Roxithromycin and formoterol fumarate particles have therefore been developed for use in multiparticulate single-drug and/or drug combination solid oral dosage forms. Roxithromycin particles at high drug loading levels may be prepared by various methods known to those skilled in the art, but the extrusion/spheronization process is particularly well-suited to preparing roxithromycin particles. Formoterol particles at low drug loading may be prepared by various methods known to those skilled in the art, but the process of spray coating formoterol fumarate onto inactive nonpareils is particularly well-suited to preparing formoterol fumarate particles. In principle, these roxithromycin and/or formoterol particles could be subsequently spray-coated to modify environmental safety, release-rate, and/or chemical interaction properties. Multiple particles filled into hard gelatin capsules and or pressed into tablets could also offer flexibility with respect to active ingredient strength(s) in the final dosage forms.

Four roxithromycin particle formulations were prepared. Table 20 shows the formulation compositions and code designations

TABLE 20

Nominal Compositions of Roxithromycin Formulation Variants

| Formula Number | Target Drug Load, % | Pellet mg per 150-mg Roxithromycin Dose | Polymer* Binder | Filler |
|---|---|---|---|---|
| 1-A | 79.0% | 189.9 | HPMC E4M | MCC |
| 2-B | 80.0% | 187.5 | HPMC E5 | MCC |
| 3-C | 85.0% | 176.5 | HPMC E4M | MCC |
| 4-D | 90.0% | 166.7 | HPMC E5 | MCC |

*HPMC is hydroxypropyl methylcellulose, MCC is microcrystalline cellulose

Three formoterol fumarate particle formulations were prepared. Table 21 shows the formulation compositions.

TABLE 21

Nominal Compositions of Formoterol Fumarate Formulation Variants

| Formula Number | Target Drug Load, % | Pellet mg per 80 µg Formoterol Fumarate Dose | Core* Type | Polymer* Binder | Coating |
|---|---|---|---|---|---|
| 6-F | 0.053% | 150.0 | Sugar | HPMC E5 | HPMC |
| 7-G | 0.053% | 150.0 | MCC | HPMC E5 | HPMC |
| 8-H | 0.053% | 150.0 | Sugar | PVP K29/32 | HPMC |

*HPMC is hydroxypropyl methylcellulose, MCC is microcrystalline cellulose, PVP is polyvinyl pyrrolidone Representative preparative methods are described below.
The steps used to prepare roxithromycin formulation 2B were as follows:
 Weigh out the roxithromycin, microcrystalline cellulose PH 101, and HPMC E5 and add to a planetary mixer (Hobart). Mix for 5 min.
 Weigh 95 g of purified water, add the water to the mixing powders over two minutes.
 Continue mixing the wet powders for 10 min, scraping the wall of the mixing bowl.
 Pass the wet mass through the LCI Bench-Top radial extruder fitted with a 1.0 mM round-hole screen. Collect the exudates in preparation of spheronization.
 Place approximately 100 g of exudate into the Caleva Bench-Top spheronizer and run for 5 to 10 minutes to round the exudates into particles.
 Continue the spheronization process until all the exudates has been processed.
 Collect the wet particles and air dry at 45° C. for 12 h The steps used to prepare roxithromycin Formulation 4D lot were as follows:
 Weigh out the roxithromycin, microcrystalline cellulose PH 101, and HPMC E5 and add to a planetary mixer (Hobart). Mix for 5 min.
 Weigh 60 g of purified water, add the water to the mixing powders over 1 min.
 Continue mixing the wet powders for 10 min, scraping the wall of the mixing bowl.

Pass the wet mass through the LCI Bench-Top radial extruder fitted with a 1.0 mM round hole screen. Collect the exudates in preparation of spheronization.

Place approximately 100 g of exudate into the Caleva Bench-Top spheronizer. Add a portion of the Cab-O-Sil to the spheronizer and run for 1 to 2 min to round the exudates into particles.

Continue the spheronization process until all the exudates has been processed.

Collect the wet particles and air dry at 45° C. for 12 h.

The steps used to prepare Formoterol Fumarate Formulation 6F were as follows:

Weigh out the Formoterol, sugar cores, and HPMC E5 (two portions) and add the cores to the fluid bed (bottom spray column).

Prepare two 7.5% HPMC solutions using the two portions of the weighed HPMC E5. Once a clear solution has been made add and mix the formoterol fumarate into one of the HPMC solutions to prepare the layering solution.

Pre-heat the sugar cores in the fluid to a product temperature of 40 to 45° C. using an inlet air temperature of 60° C.

Begin spraying the layering solution onto the cores using an atomizing air pressure of 1 to 1.5 bar. Adjust the inlet air temperature to maintain a product temperature of 36 to 43° C.

Once all the layering solution has been applied dry the particles to a product temperature of approximately 45° C.

Begin spraying the second HPMC solution (coating solution) onto the layered cores using an atomizing air pressure of 1 to 1.5 bar. Adjust the inlet air temperature to maintain a product temperature of 36 to 43° C.

Once all the coating solution has been applied dry the layered coated particles to a product temperature of approximately 45 to 50° C.

The steps used to prepare Formoterol Fumarate Formulation 7G were as follows:

Weigh out the formoterol fumarate, microcrystalline cellulose cores, and HPMC E5 (two portions) and add the cores to the fluid bed (bottom spray column).

Prepare two 7.5% HPMC solutions using the two portions of the weighed HPMC E5. Once a clear solution has been made add and mix the formoterol fumarate into one of the HPMC solution to prepare the layering solution.

Pre-heat the MCC cores in the fluid to a product temperature of 40 to 45° C. using an inlet air temperature of 60° C.

Begin spraying the layering solution onto the cores using an atomizing air pressure of 1 to 1.5 bar. Adjust the inlet air temperature to maintain a product temperature of 36 to 43° C.

Once all the layering solution has been applied dry the particles to a product temperature of approximately 45° C.

Begin spraying the second HPMC solution (coating solution) onto the layered cores using an atomizing air pressure of 1 to 1.5 bar. Adjust the inlet air temperature to maintain a product temperature of 36 to 43° C.

Once all the coating solution has been applied dry the layered coated particles to a product temperature of approximately 45 to 50° C.

The steps used to prepare Formoterol Fumarate Formulation 8H were as follows:

Weigh out the formoterol fumarate, sugar cores, Povidone, and HPMC E5 and add the cores to the fluid bed (bottom spray column).

Prepare a 7.5% HPMC solution (coating solution).

Prepare a 7.5% Povidone solution using a 50/50 mixture of purified water and ethanol. Once a clear solution has been made add and mix the formoterol fumarate into the solution to prepare the layering solution.

Pre-heat the sugar cores in the fluid to a product temperature of 40 to 45° C. using an inlet air temperature of 60° C.

Begin spraying the layering solution onto the cores using an atomizing air pressure of 1 to 1.5 bar. Adjust the inlet air temperature to maintain a product temperature of 36 to 43° C.

Once all the layering solution has been applied dry the particles to a product temperature of approximately 45° C.

Begin spraying the HPMC solution (coating solution) onto the layered cores using an atomizing air pressure of 1 to 1.5 bar. Adjust the inlet air temperature to maintain a product temperature of 36 to 43° C.

Once all the coating solution has been applied dry the layered coated particles to a product temperature of approximately 45 to 50° C.

The amount of roxithromycin in each of the prepared formulations was determined by HPLC. Table 22 shows the results of the potency testing, expressed as the mg of roxithromycin present in 100 mg of particles, and also as the mg of particles required to provide a 150 mg dose of roxithromycin. The table shows that roxithromycin particles can be prepared over a range of loading levels and that the amount of particles required to produce a 150 mg roxithromycin does is well within the range of particle mass that could be incorporated into a capsule or tablet dosage form of reasonable size.

TABLE 22

Potency Determinations for Roxithromycin Formulations

| Formulation | Roxithromycin mg/100 mg particle | mg particle/150 mg Roxithromycin dose |
|---|---|---|
| -1A | 77.6 | 193 |
| -2B | 78.2 | 192 |
| -3C | 82.8 | 181 |
| -4D | 87.9 | 171 |

The amount of formoterol fumarate in each of the prepared formulations was determined by HPLC. Table 23 shows the results of the potency testing, expressed as the weight (µg) of formoterol fumarate present in 100 mg of particles, and also as the weight (mg) of particles required to provide an 80 µg dose of formoterol fumarate. The table shows that formoterol fumarate particles can be prepared over a range of loading levels and that the amount of particles required to produce an 80 µg formoterol fumarate dose is well within the range of particle mass that could be incorporated into a capsule or tablet dosage form of reasonable size. The table also shows satisfactory uniformity in the content of formoterol fumarate between samples.

TABLE 23

Potency Determinations for Formoterol Fumarate Formulation Variants

| Formulation Variant* | Formoterol Weight (μg) per 100 mg Micro-particles | | | | Mean Micro-particle Weight (mg) per 80 μg Formoterol Fumarate Dose |
|---|---|---|---|---|---|
| | Sample 1 | Sample 2 | Mean | % RSD | |
| -6F | 2.50 | 2.35 | 2.43 | 4% | 330 |
| -7G | 1.85 | 2.0 | 1.93 | 6% | 416 |
| -8H | 5.95 | 5.75 | 5.85 | 2% | 137 |

The dissolution profiles of the roxithromycin particle formulations were determined by HPLC using the USP I method at 37° C. and either pH 6, 20 mM citrate buffer or pH 2.7 aqueous HCl as the dissolution media. The pH 6 medium approximates the pH of the enteric compartment and pH 2.7 approximates the upper limit of the pH of the gastric compartment. Determining roxithromycin dissolutions profiles at pH<2.7 is impractical because roxithromycin undergoes acid-catalyzed degradation very rapidly per Zhang et al (J Pharm Sci 93:1300-9, 2004).

Table 24 shows the results of the dissolution testing at pH 2.7 and Table 25 shows the dissolution data f the pH 6 medium. At pH 2.7, the roxithromycin particle formulations released approximately 50% of added roxithromycin within 1 hour. At longer time intervals, decreasing roxithromycin recovery values indicate roxithromycin degradation (approximately 5% per hour) concomitant with release. At pH 6, somewhat less than 50% of added roxithromycin was released in approximately 2 hours and approximately 70% was released over 18 hours. These dissolution data indicate that the roxithromycin particle formulations would release approximately half of the added roxithromycin rapidly while resident in the gastric compartment for a typical 1 hour gastric emptying period, and the remainder more slowly while resident in the enteric compartment.

TABLE 24

% of Added Roxithromycin Recovered Versus Time in pH 2.7 Dissolution Medium

| Time, h | % of Added[†] Roxithromycin Recovered for Formulation Variant* = | | | |
|---|---|---|---|---|
| | -1A | -2B | -3C | -4D |
| 0.083 | 28.3% | 24.9% | 24.6% | 26.1% |
| 0.17 | 33.3% | 40.5% | 31.0% | 36.0% |
| 0.5 | | 44.6% | 42.1% | 49.6% |
| 1 | 52.5% | 52.7% | 49.7% | 43.3% |
| 2 | 59.5% | 59.4% | 56.3% | 63.8% |
| 4 | 51.8% | 54.5% | 54.2% | 53.9% |
| 6 | 43.6% | 43.3% | 42.1% | 42.3% |

[†] % Recovery based on mg micro-particles added to dissolution medium and mean μg formoterol per 100 mg micro-particle load values taken from Table 22

TABLE 25

% of Added Roxithromycin Recovered Versus Time in pH 6 Dissolution Medium

| Time, h | % of Added Roxithromycin Recovered[†] for Formulation Variant = | | | |
|---|---|---|---|---|
| | -1A | -2B | -3C | -4D |
| 0.08 | 7 | 7 | 8 | 5 |
| 0.17 | 13 | 9 | 14 | 10 |
| 0.25 | 19 | 14 | 18 | 16 |
| 0.33 | 24 | 19 | 24 | 21 |
| 0.50 | 31 | 26 | 19 | 16 |
| 1.0 | 28 | 28 | 28 | 31 |
| 2.0 | | 44 | 44 | 51 |
| 18 | 77 | 73 | 71 | 71 |

[†] % Recovery based on mg micro-particles added to dissolution medium and mean μg formoterol per 100 mg micro-particle load values taken from Table 22

The dissolution rates of the formoterol fumarate particle formulations was determined by the USP I method using pH 6, 20 mM citrate buffer as the medium (to approximate the pH of the gut). Formoterol fumarate concentrations were determined by HPLC. Table 26 shows the results of the dissolution testing. The table determined that ≧75% of the added formoterol fumarate was released within approximately 5 minutes. The tested dosage forms are therefore suitable for an immediate-release, solid oral dosage form.

TABLE 26

% of Added Formoterol Fumarate Recovered Versus Time in pH 6 Dissolution Medium

| Time, h | % of Added Formoterol Recovered[†] for Formulation Variant = | | |
|---|---|---|---|
| | -6F | -7G | -8H |
| 5 | 79% | 79% | 85% |
| 10 | 89% | 82% | 87% |
| 20 | 99% | 82% | 85% |
| 30 | 98% | 85% | 90% |
| 60 | 94% | 92% | 90% |
| 120 | 98% | 87% | 90% |
| 1080 | 96% | 90% | 90% |

[†] % Recovery based on mg micro-particles added to dissolution medium and mean μg formoterol per 100 mg micro-particle load values taken from

7 CONCLUSION

Although various specific embodiments and examples have been described herein, those having ordinary skill in the art will understand that many different implementations of the invention can be achieved without departing from the spirit or scope of this disclosure. For example, the roxithromycin used in the above-described examples can be replaced with other macrolides, such as, but not limited to, clarithromycin and azithromycin. Still other variations will be clear to those having ordinary skill in the art.

What is claimed:

1. A method for treating cancer-related cachexia in a mammal, comprising administering to such mammal a macrolide and a $\beta_2$-agonist in combination, wherein said macrolide and said $\beta_2$-agonist are administered in the same pharmaceutically acceptable carrier, said macrolide is roxithromycin, said roxithromycin is administered at a dose of between about 50 mg/d and about 200 mg/d, and wherein said $\beta_2$-agonist is formoterol fumarate.

2. The method of claim 1, wherein said formoterol fumarate is administered at a dose between about 5 μg/d and about 500 μg/d.

3. The method of claim 2, wherein said formoterol fumarate is administered at a dose between about 5 μg/d and about 240 μg/d.

* * * * *